United States Patent
Ando

(10) Patent No.: US 10,215,718 B2
(45) Date of Patent: *Feb. 26, 2019

(54) ELECTRON BEAM INSPECTION APPARATUS AND ELECTRON BEAM INSPECTION METHOD

(71) Applicant: NuFlare Technology, Inc., Yokohama-shi (JP)

(72) Inventor: Atsushi Ando, Edogawa-ku (JP)

(73) Assignee: NuFlare Technology, Inc., Yokohama-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/623,416

(22) Filed: Jun. 15, 2017

(65) Prior Publication Data

US 2018/0024082 A1    Jan. 25, 2018

(30) Foreign Application Priority Data

Jul. 25, 2016 (JP) ................. 2016-145619

(51) Int. Cl.
*G01N 23/22* (2018.01)
*G01N 23/2204* (2018.01)
*G01N 23/2251* (2018.01)

(52) U.S. Cl.
CPC ..... *G01N 23/2204* (2013.01); *G01N 23/2251* (2013.01)

(58) Field of Classification Search
CPC ............ G01N 23/2204; G01N 23/2251; H01J 37/045; H01J 37/26; H01J 37/28; H01J 37/3171; H01J 37/3177
See application file for complete search history.

(56) References Cited

U.S. PATENT DOCUMENTS

| 6,133,986 A | 10/2000 | Johnson |
| 8,351,020 B2 | 1/2013 | Sandstrom |
| 2005/0214958 A1* | 9/2005 | Nakasuji ............ G01N 23/225 438/14 |
| 2009/0114818 A1* | 5/2009 | Casares ............... H01J 37/045 250/307 |

(Continued)

FOREIGN PATENT DOCUMENTS

| JP | 2003-188221 | 7/2003 |
| JP | 2012-510085 | 4/2012 |

(Continued)

*Primary Examiner* — David E Smith
(74) *Attorney, Agent, or Firm* — Oblon, McClelland, Maier & Neustadt, L.L.P.

(57) ABSTRACT

An electron beam inspection apparatus includes a stage to mount a substrate to be inspected thereon and to be continuously movable, an electron beam column, while the stage continuously moves, to scan the substrate by irradiating the substrate with multi-beams composed of a plurality of first electron beams in a plurality of beam rows, in each of which corresponding beams of the plurality of first electron beams are arranged at a same pitch in a straight line, such that the center of each of irradiation regions irradiated with the multi-beams does not overlap with the other irradiation regions in a movement direction of the stage, and a detector to detect a secondary electron emitted from the substrate due to irradiation of the multi-beams on the substrate.

10 Claims, 19 Drawing Sheets

(56) References Cited

U.S. PATENT DOCUMENTS

| | | | | |
|---|---|---|---|---|
| 2010/0320382 A1* | 12/2010 | Almogy | ........... | H01J 37/05 |
| | | | | 250/307 |
| 2011/0272576 A1* | 11/2011 | Otaki | ........... | B82Y 10/00 |
| | | | | 250/306 |
| 2012/0241606 A1* | 9/2012 | Han | ........... | G01N 23/2251 |
| | | | | 250/307 |
| 2013/0056647 A1* | 3/2013 | Yoshikawa | ........... | H01J 37/3026 |
| | | | | 250/400 |
| 2013/0299697 A1* | 11/2013 | Enyama | ........... | H01J 37/12 |
| | | | | 250/307 |
| 2014/0175303 A1* | 6/2014 | Touya | ........... | H01J 37/3026 |
| | | | | 250/398 |
| 2018/0031498 A1* | 2/2018 | Shiratsuchi | ........... | G01N 23/2251 |

FOREIGN PATENT DOCUMENTS

| | | |
|---|---|---|
| JP | 2014-521193 | 4/2014 |
| JP | 2015-133400 | 7/2015 |
| KR | 10-2016-0065042 | 6/2016 |

\* cited by examiner

Movement Direction

Two Times T / P

Movement Direction

Eight Times T / P

Scanning range
when aperture is not rotated when aperture is rotated 11 beams 110 beams

ELECTRON BEAM INSPECTION APPARATUS AND ELECTRON BEAM INSPECTION METHOD

CROSS-REFERENCE TO RELATED APPLICATION

This application is based upon and claims the benefit of priority from the prior Japanese Patent Application No. 2016-145619 filed on Jul. 25, 2016 in Japan, the entire contents of which are incorporated herein by reference.

BACKGROUND OF THE INVENTION

Field of the Invention

Embodiments of the present invention relate generally to an electron beam inspection apparatus, and an electron beam inspection method. More specifically, for example, embodiments of the present invention relate to an inspection apparatus which inspects a pattern by acquiring a secondary electron image of an emitted image of the pattern irradiated with electron multi-beams.

Description of Related Art

In recent years, with the advance of high integration and large capacity of large-scale integration (LSI) circuits, the line width (critical dimension) required for circuits of semiconductor elements is becoming progressively narrower. Such semiconductor elements are manufactured by circuit formation of exposing and transferring a pattern onto a wafer by means of a reduced projection exposure apparatus known as a stepper while using an original or "master" pattern (also called a mask or a reticle, hereinafter generically referred to as a mask) with a circuit pattern formed thereon.

Since LSI manufacturing requires a tremendous amount of manufacturing cost, it is crucial to improve its yield. However, as typified by a 1-gigabit DRAM (Dynamic Random Access Memory), the scale of patterns configuring an LSI has become on the order of nanometers from submicrons. In recent years, with miniaturization of dimensions of LSI patterns formed on a semiconductor wafer, dimension to be detected as a pattern defect has become extremely small. Therefore, a pattern inspection apparatus for inspecting defects of ultrafine patterns transferred and exposed onto a semiconductor wafer needs to be more highly accurate. Further, one of major factors that decrease the yield of the LSI manufacturing is due to pattern defects on the mask used for exposing and transfer printing an ultrafine pattern onto a semiconductor wafer by the photolithography technology. Therefore, a pattern inspection apparatus for inspecting defects on a transfer mask used in manufacturing LSI needs to be more highly accurate.

As an inspection method, there is known a method of comparing an optical image obtained by imaging a pattern formed on a substrate (target object or "sample") such as a semiconductor wafer and a lithography mask at a predetermined magnification by using a magnification optical system with design data or an optical image obtained by imaging the same pattern on the target object. For example, the methods described below are known as pattern inspection methods: the "die-to-die inspection" method that compares data of optical images of identical patterns at different positions on the same mask; and the "die-to-database inspection" method that inputs, into an inspection apparatus, writing data (design pattern data) generated by converting pattern-designed CAD data to a writing apparatus specific format to be input to the writing apparatus when a pattern is written on the mask, generates a design image data (reference image) based on the input writing data, and compares the generated design image with an optical image (serving as measured target data) obtained by imaging the pattern. In such inspection methods for use in the inspection apparatus, a substrate to be inspected (an inspection substrate or "object" to be examined) is placed on the stage so that a light flux may scan the substrate (target object) as the stage moves in order to perform an inspection. Specifically, the substrate to be inspected is irradiated with a light flux from the light source through the illumination optical system. The light transmitted through the inspection substrate or reflected therefrom forms an image on a sensor through the optical system. The image captured by the sensor is transmitted as measured target data to the comparison circuit. After performing positioning between images, the comparison circuit compares measured target data with reference data in accordance with an appropriate algorithm, and determines that there exists a pattern defect if the compared data are not identical.

The pattern inspection apparatus described above acquires an optical image by irradiating an inspection substrate with a laser beam in order to capture a transmission image or a reflection image of a pattern formed on the substrate. On the other hand, there has been developed an inspection apparatus which acquires a pattern image by irradiating an inspection substrate with multiple beams composed of a plurality of electron beams in an array of a plurality of beam rows in each of which beams are arranged in a straight line at the same pitch in order to detect a secondary electron corresponding to each beam emitted from the inspection substrate. This pattern inspection apparatus using an electron beam (e.g., electron multi-beams), scans each small region of the inspection substrate with beams so as to detect a secondary electron. In that case, a so-called "step and repeat" operation is performed in which the position of the substrate to be inspected is fixed during beam scanning, and, after the scanning, the substrate to be inspected is moved to a next region. By using multiple beams in an array of a plurality of beam rows in each of which beams are arranged in a straight line at the same pitch, a large number of beams can be arranged within a limited region, and therefore, it becomes possible to scan many small regions at one time simultaneously. Accordingly, improvement of throughput is expected. However, in the step and repeat operation, the settling time (overhead time) until the stage position is stabilized is needed for each stage movement. Since one scanning range (small region) is small, an enormous number of times of stepping of the stage is necessary to scan the entire substrate. Therefore, unnecessary time not used for scanning occurs to be the amount of a time obtained by multiplying the settling time by the number of times of stepping. Even when performing scanning on the substrate by using multi-beams, there is an estimate that, for example, unnecessary time for scanning of 80 hours or more occurs for one substrate.

Then, in order to improve the throughput of the inspection apparatus, it is examined to change the stage movement method from the step and repeat operation method to the continuous movement method which does not require a settling time for each step. However, when performing scanning with multi-beams in an array, although the settling time is made unnecessary in the continuous movement method, instead, since the same small region is sequentially sent to scan ranges of a plurality of beams arranged in a line in the movement direction, unnecessary scanning is repeated for small regions whose pattern images have already been acquired. Therefore, still, it does not lead to improvement of the throughput.

Here, another inspection apparatus is examined which performs scanning on a target object while continuously moving the stage in the y direction, using multi-beams in which each beam is arranged along the circumference to be at an equal interval with respect to the x direction (e.g., refer to Japanese Patent Application Laid-open No. 2003-188221). However, with this method, since the portion where beams can be arranged is restricted on the circumference, not only it is not possible to increase the number of beams, but it is even difficult to apply this method to multi-beams in an array of a plurality of beam rows in each of which beams are arranged in a straight line at the same pitch.

BRIEF SUMMARY OF THE INVENTION

According to one aspect of the present invention, an electron beam inspection apparatus includes a stage configured to mount a substrate to be inspected thereon and to be continuously movable, an electron beam column configured, while the stage continuously moves in a predetermined direction, to scan the substrate by irradiating the substrate with multi-beams composed of a plurality of first electron beams in a plurality of beam rows, in each of which corresponding beams of the plurality of first electron beams are arranged at a same pitch in a straight line, such that a center of each of irradiation regions irradiated with the multi-beams does not overlap with other irradiation regions of the irradiation regions in a direction parallel to a movement direction of the stage, and a detector configured to detect a secondary electron emitted from the substrate due to irradiation of the multi-beams on the substrate, wherein the electron beam column scans the substrate by deflecting the multi-beams such that a size in the movement direction of the stage, with respect to each of deflection regions for deflecting the multi-beams, differs from a size in a direction orthogonal to the movement direction of the stage.

According to another aspect of the present invention, an electron beam inspection method includes scanning, while a stage on which a substrate is placed continuously moves, the substrate with multi-beams composed of a plurality of first electron beams in a plurality of beam rows, in each of which corresponding beams of the plurality of first electron beams are arranged at a same pitch in a straight line, such that a center of each of irradiation regions of the multi-beams does not overlap with other irradiation regions of the irradiation regions in a direction parallel to a movement direction of the stage, and detecting a secondary electron emitted from the substrate due to irradiation of the multi-beams on the substrate, wherein the scanning the substrate is performed by deflecting the multi-beams such that a size in the movement direction of the stage, with respect to each of deflection regions for deflecting the multi-beams, differs from a size in a direction orthogonal to the movement direction of the stage.

DETAILED DESCRIPTION OF THE INVENTION

Embodiments below describe an electron beam inspection apparatus and method which can increase the throughput in pattern inspection using multi-beams in an array of a plurality of beam rows in each of which beams are arranged in a straight line at the same pitch.

First Embodiment

Figure 1:
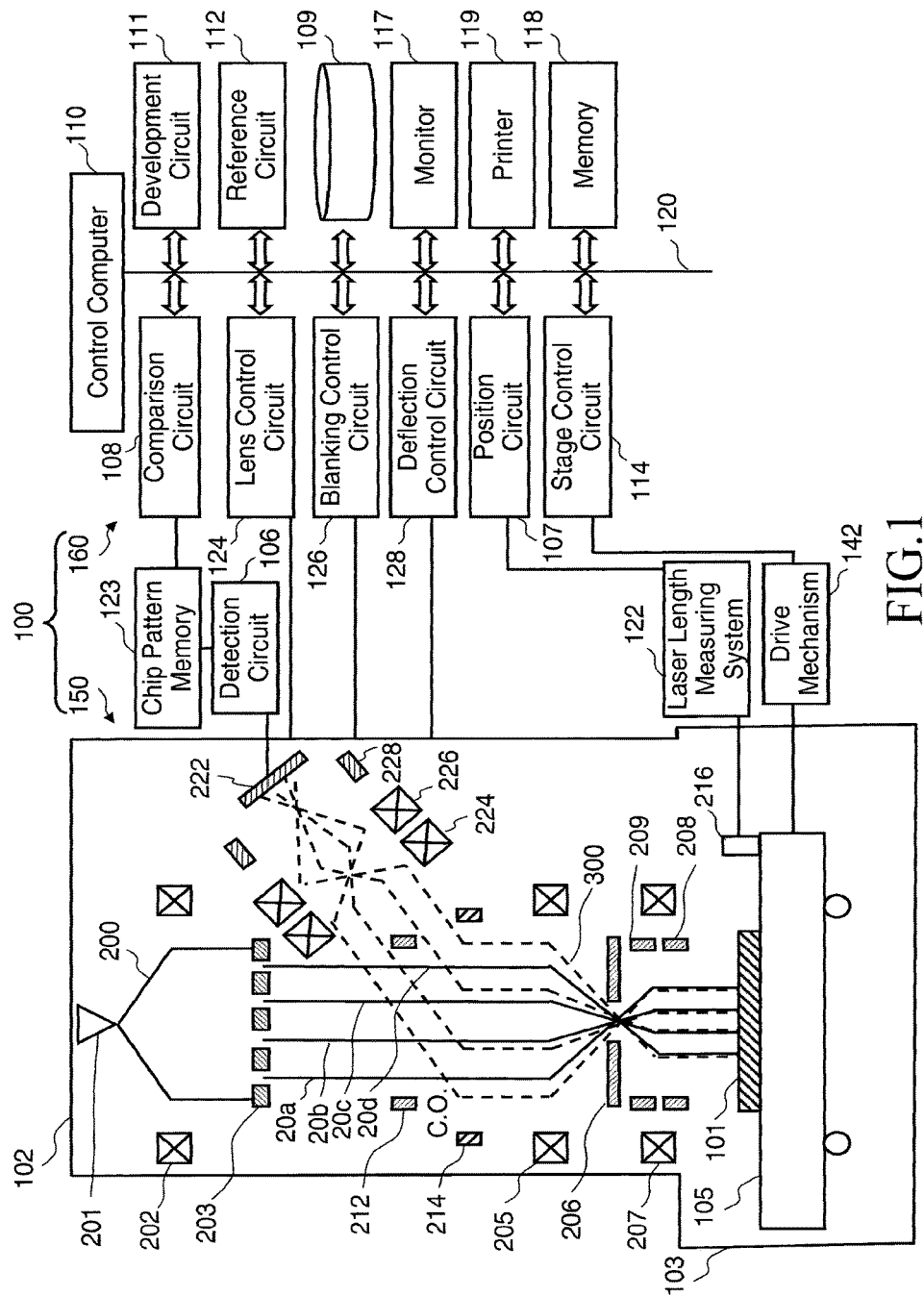
FIG. 1 shows a configuration of a pattern inspection apparatus according to a first embodiment.

FIG. 1 shows a configuration of a pattern inspection apparatus according to a first embodiment. In FIG. 1, an inspection apparatus 100 for inspecting patterns formed on the substrate is an example of a multi electron beam inspection apparatus. The inspection apparatus 100 includes an electron optical image acquisition mechanism 150 and a control system circuit 160 (control circuit). The electron optical image acquisition mechanism 150 includes an electron beam column 102 (electron optical column), an inspection chamber 103, a detection circuit 106, a chip pattern memory 123, a stage drive mechanism 142, and a laser length measurement system 122. In the electron beam column 102, there are arranged an electron gun 201, an illumination lens 202, a shaping aperture array substrate 203, a reducing lens 205, a limiting aperture substrate 206, an objective lens 207, a main deflector 208, a sub deflector 209, a common blanking deflector 212, a beam separator 214, projection lenses 224 and 226, a deflector 228, and a multi-detector 222.

In the inspection chamber 103, there is arranged an XY stage 105 which is movable at least in the x-y plane. On the XY stage 105, there is placed a substrate 101 on which a plurality of chip patterns to be inspected are formed. The substrate 101 may be an exposure mask or a semiconductor substrate such as a silicon wafer. The substrate 101 is placed, on the XY stage 105, with its pattern forming surface facing upward, for example. On the XY stage 105, there is arranged a mirror 216 which reflects a laser beam for measuring a laser length emitted from the laser length measurement system 122 arranged outside the inspection chamber 103. The multi-detector 222 is connected, at the outside of the electron beam column 102, to the detection circuit 106. The detection circuit 106 is connected to the chip pattern memory 123.

In the control system circuit 160, a control computer 110 is connected, through a bus 120, to a position circuit 107, a comparison circuit 108, a development circuit 111, a reference circuit 112, a stage control circuit 114, a lens control circuit 124, a blanking control circuit 126, a deflection control circuit 128, a storage device 109 such as a magnetic disk drive, a monitor 117, a memory 118, and a printer 119. The chip pattern memory 123 is connected to the comparison circuit 108. The XY stage 105 is driven by the drive mechanism 142 under the control of the stage control circuit 114. The XY stage 105 can be moved by a drive system, in the drive mechanism 142, such as a three-axis (X, Y, and θ) motor, which drives the stage in the directions of x, y, and θ. For example, a step motor can be used as each of these X, Y, and θ motors (not shown). The XY stage 105 is movable in the horizontal direction and the rotation direction by the motors of the X-axis, Y-axis, and θ-axis. The movement position of the XY stage 105 is measured by the laser length measurement system 122, and supplied (transmitted) to the position circuit 107. The laser length measurement system 122 measures the position of the XY stage 105 by receiving a reflected light from the mirror 216, based on the principle of laser interferometry.

A high voltage power supply circuit (not shown) is connected to the electron gun 201. The high voltage power supply circuit applies an acceleration voltage to between a filament and an extraction electrode (anode electrode) (which are not shown) in the electron gun 201. In addition to the applying the acceleration voltage, by applying a predetermined voltage to a Wehnelt electrode, and heating a cathode at a predetermined temperature, electrons emitted from the cathode are accelerated to become electron beams which are to be emitted. For example, electromagnetic lenses are used as the illumination lens 202, the reducing lens 205, the objective lens 207, and the projection lenses 224 and 226, and all of them are controlled by the lens control circuit 124. The beam splitter 214 is also controlled by the lens control circuit 124. The common blanking deflector 212 and the deflector 228 are individually configured by at least two electrodes, and controlled by the blanking control circuit 126. The main deflector 208 and the sub deflector 209 are individually configured by at least four electrodes, and controlled by the deflection control circuit 128.

In the case of the substrate 101 being a semiconductor wafer on which a plurality of chip (die) patterns are formed, pattern data of the chip (die) pattern is input from the outside of the inspection apparatus 100 to the storage device 109 to be stored therein.

FIG. 1 shows configuration elements necessary for describing the first embodiment. It should be understood that other configuration elements generally necessary for the inspection apparatus 100 may also be included therein.

Figure 2:
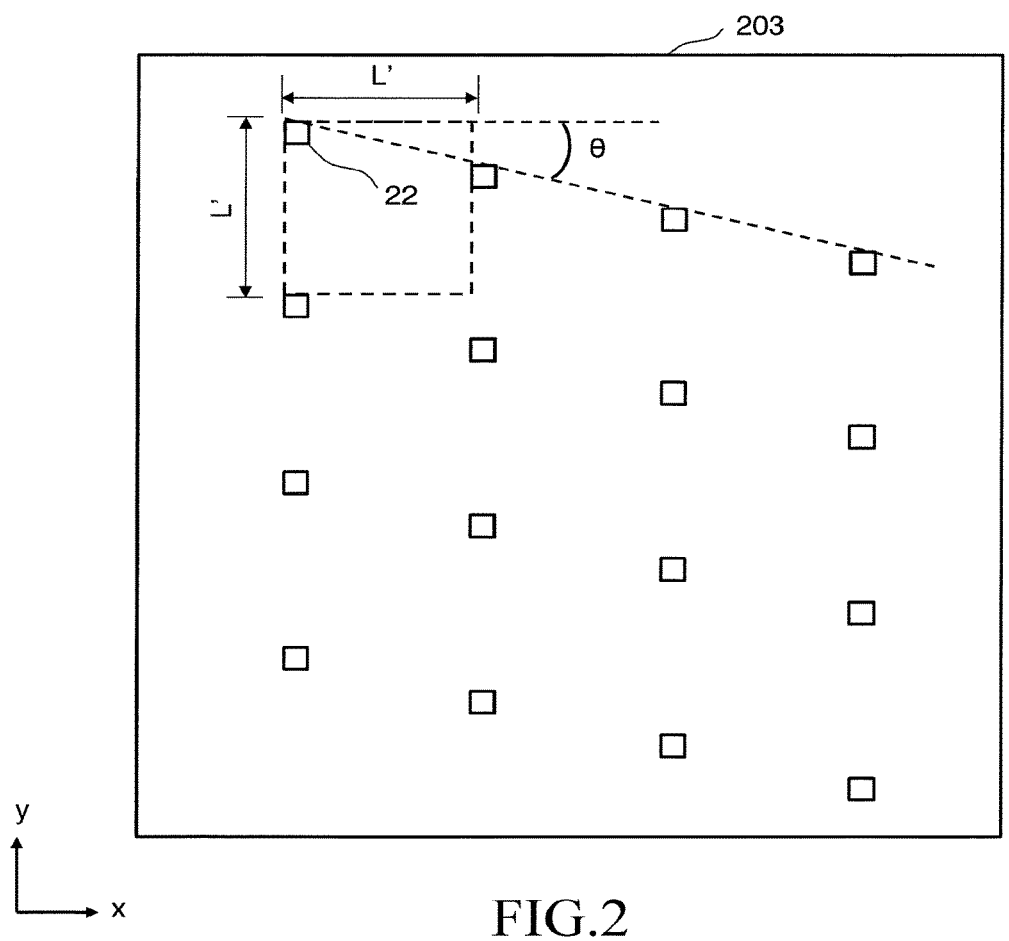
FIG. 2 is a conceptual diagram showing a configuration of a shaping aperture array substrate according to the first embodiment.

FIG. 2 is a conceptual diagram showing a configuration of a shaping aperture array substrate according to the first embodiment. As shown in FIG. 2, holes (openings) 22 of m columns wide (width in the x direction) and n rows long (length in the y direction) (each of n and m is an integer of 2 or more) are two-dimensionally formed in the x and y directions at a predetermined arrangement pitch L' in the shaping aperture array substrate 203. In the case of the reduction ratio of multi-beams being "a" times (in the case of irradiating the substrate 101 with multi-beams whose diameter has been reduced to 1/a)), L'=aL. In that case, let L be the pitch between beams of the multi-beams with respect to the x and y directions on the substrate 101. In the first embodiment, m holes 22 aligned in the x direction are formed with being shifted by L'/m in the −y direction (or +y direction) in order. In the example of FIG. 2, four holes 22 aligned in the x direction are formed with being shifted by L'/4 in the −y direction in order. With such arrangement, for example, a plurality of holes 22 are formed two-dimensionally such that they are arranged at the same pitch in a plurality of virtual straight lines aligned in parallel to each other at the same interval in the y direction. In the example of FIG. 2, a plurality of holes 22 are arranged at the same pitch in a plurality of straight lines inclined clockwise with respect to the x axis by the angle $\theta(=\tan^{-1}(1/m))$ Alternatively, a plurality of holes 22 are arranged at the same pitch in a plurality of straight lines parallel to the y axis, and each of the holes 22 arranged in each line is shifted by L'/4 in order. Thus, the y direction position of each of m holes 22 aligned in the movement direction (here, −x direction) of the XY stage 105 is shifted by L'/m in order. Thereby, all the holes 22 formed in the shaping aperture array substrate 203 can be formed such that they do not overlap with each other in the movement direction (−x direction) toward which the XY stage 105 continuously moves for scanning, or/and in the inspection direction that moves in the x direction along with the movement of the XY stage 105. Needless to say, the size of the hole 22 is sufficiently smaller than L'/m. Next, the operation of the electron optical image acquisition mechanism 150 in the inspection apparatus 100 will be described.

Figure 3:
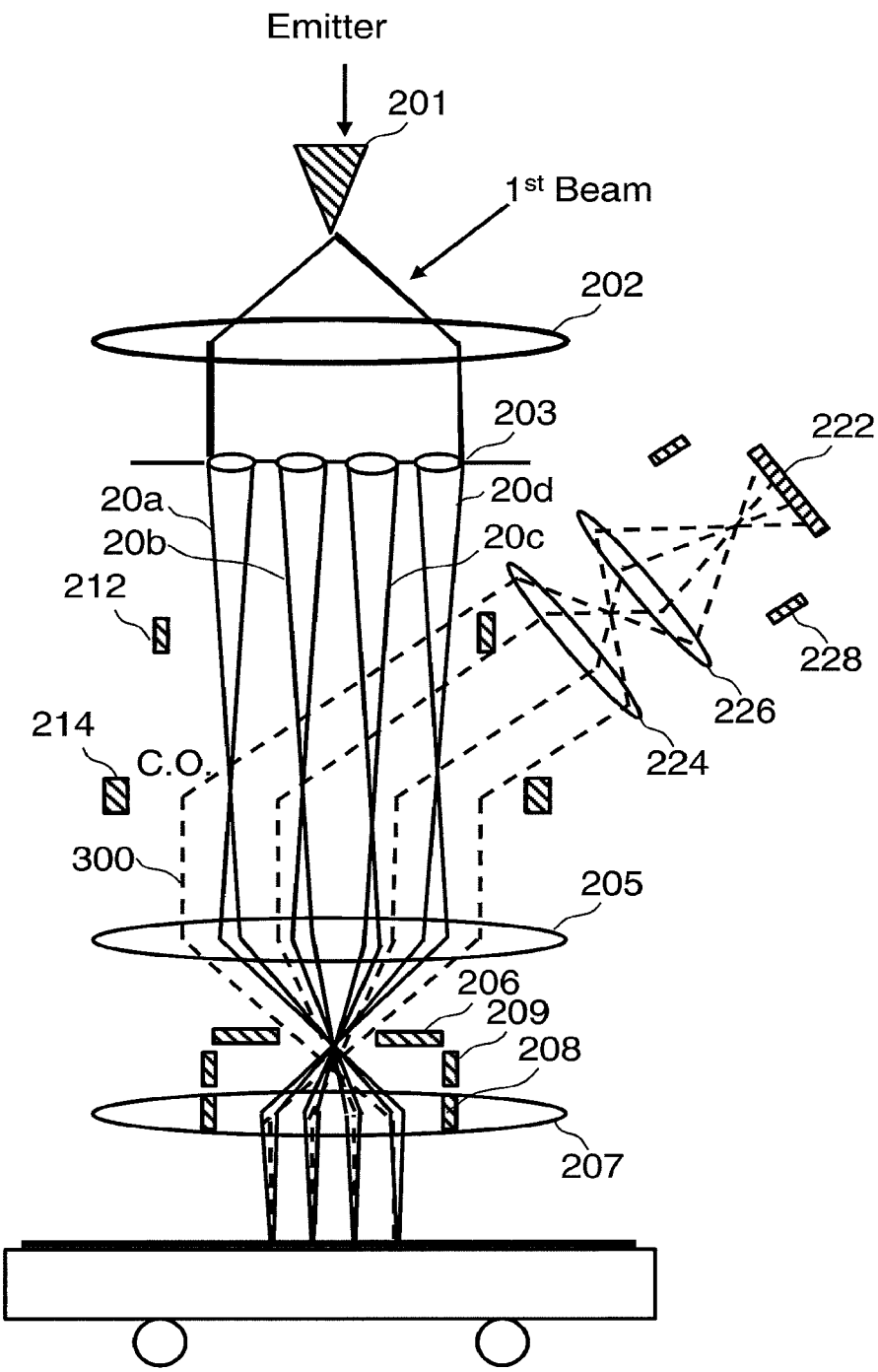
FIG. 3 illustrates a beam trajectory in an inspection apparatus according to the first embodiment.

FIG. 3 illustrates a beam trajectory in an inspection apparatus according to the first embodiment. An electron beam 200 (second electron beam) emitted from the electron gun 201 (emission source) almost perpendicularly (e.g., vertically) illuminates the whole of the shaping aperture array substrate 203 by the illumination lens 202. In the shaping aperture array substrate 203, there are formed a plurality of quadrangular holes (openings) 22 as shown in FIG. 2, and the region including all the plurality of holes 22 is irradiated with the electron beam 200. For example, a plurality of circular electron beams (multi-beams) (a plurality of first electron beams) 20a to 20d (solid lines in FIGS. 1 and 3) are formed by letting portions of the electron beam 200, which irradiates the positions of a plurality of holes 22, individually pass through a corresponding one of the plurality of holes 22 in the shaping aperture array substrate 203. Then, the multi-beams 20a to 20d form a crossover (C.O.). After having passed through the beam separator 214 arranged at the crossover position of the multi-beams 20, the multi-beams 20a to 20d are reduced by the reducing lens 205, and go toward the hole in the center of the limiting aperture substrate 206. At this stage, when being collectively deflected by the common blanking deflector 212 placed between the shaping aperture array substrate 203 and the reducing lens 205, the entire multi-beams 20a to 20d deviate from the hole in the center of the limiting aperture substrate 206 so as to be blocked by the limiting aperture substrate 206. On the other hand, the multi-beams 20a to 20d which were not deflected by the common blanking deflector 212 pass through the hole in the center of the limiting aperture substrate 206 as shown in FIG. 1. Blanking control is provided by ON/OFF of the common blanking deflector 212 to collectively control ON/OFF of beams. Thus, the limiting aperture substrate 206 blocks the multi-beams 20a to 20d which were deflected to be in the OFF condition by the common blanking deflector 212. Then, the multi-beams 20a to 20d are formed by the beams having been made during a period from becoming beam ON to becoming beam OFF and having passed through the limiting aperture substrate 206. The multi-beams 20a to 20d having passed through the limiting aperture substrate 206 are focused by the objective lens 207 to be a pattern image (beam diameter) of a desired reduction ratio. Then, the whole of the multi-beams 20 having passed through the limiting aperture substrate 206 are collectively deflected in the same direction by the main deflector 208 and the sub deflector 209 in order to irradiate respective beam irradiation positions on the substrate 101. In such a case, the main deflector 208 collectively deflects the entire multi-beams 20 so that a reference position of a unit inspection region to be scanned by each beam, to be described later, may be individually irradiated, and also, tracking deflection is performed to follow the movement of the XY stage 105. Then, the sub deflector 209 collectively deflects the entire multi-beams 20 so that each beam may scan a corresponding unit inspection region. Ideally, the multi-beams 20 irradiating at a time are aligned at the pitch obtained by multiplying the arrangement pitch aL of a plurality of holes 22 in the shaping aperture array substrate 203 by a desired reduction ratio (1/a) described above. Thus, the electron beam column 102 irradiates the substrate 101 with two-dimensional m×n multi-beams 20 at a time. A flux of secondary electrons (multi-secondary electrons 300) (dotted lines in FIGS. 1 and 3) corresponding to each beam of the multi-beams 20 is emitted from the substrate 101 due to irradiation of the multi-beams 20 at desired positions on the substrate 101.

The multi-secondary electrons 300 emitted from the substrate 101 are refracted to the central side of the multi-secondary electrons 300 by the objective lens 207, and advance toward the hole in the center of the limiting aperture substrate 206. The multi-secondary electrons 300 having passed through the limiting aperture substrate 206 are refracted almost parallel to the optical axis by the reducing lens 205, and advance to the beam separator 214.

The beam separator 214 generates an electric field and a magnetic field to be orthogonal to each other in the plane perpendicular to the traveling direction (optical axis) of the multi-beam 20. The electric field affects in a fixed direction regardless of the traveling direction of electrons. In contrast, the magnetic field affects in accordance with Fleming's left-hand rule. Therefore, the direction of force acting on electrons can be changed depending on an entering direction of an electron. With respect to the multi-beams 20 (primary electron beam) entering the beam separator 214 from the upper side, since the force due to the electric field and the force due to the magnetic field cancel each other, the multi-beams 20 go straight downward. On the other hand, with respect to the multi-secondary electrons 300 entering the beam separator 214 from the lower side, since both the force due to the electric field and the force due to the magnetic field affect in the same direction, the multi-secondary electrons 300 are bent obliquely upward.

The multi-secondary electrons 300 bent obliquely upward are projected onto the multi-detector 222, with being refracted by the projection lenses 224 and 226. The multi-detector 222 detects the projected multi-secondary electrons 300. The multi-detector 222 includes a diode type two-dimensional sensor (not shown). Then, at the position of the diode type two-dimensional sensor corresponding to each beam of the multi-beams 20, each secondary electron of the multi-secondary electrons 300 collides with the diode type two-dimensional sensor so as to generate an electron. Then, secondary electron image data is generated for each pixel to be described later. When the multi-detector 222 does not detect the multi-secondary electrons 300, it is sufficient to make the multi-secondary electrons 300 not reach the light receiving surface by performing blanking deflection of the multi-secondary electrons 300 by the deflector 228.

Figure 4:
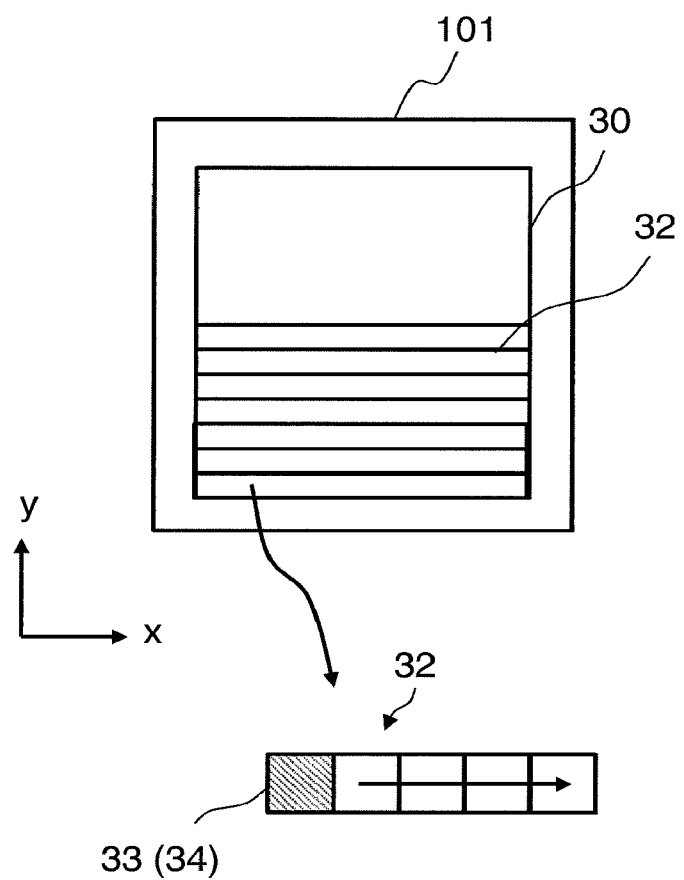
FIG. 4 is a conceptual diagram illustrating an example of a scanning operation according to the first embodiment.

FIG. 4 is a conceptual diagram illustrating an example of a scanning operation according to the first embodiment. As shown in FIG. 4, for example, an inspection region 30 of the substrate 101 is virtually divided into a plurality of strip-shaped stripe regions 32 by a predetermined width in the y direction. Preferably, for example, an exposure mask substrate is used as the substrate 101. For example, the inspection region 30 is virtually divided into a plurality of strip-shaped stripe regions 32 by a width equal to a natural multiple (or "natural number multiple") of the width of an irradiation region 34 which can be irradiated with one-shot irradiation of the entire multi-beams 20. In the case of FIG. 4, the inspection region 30 is virtually divided into a plurality of strip-shaped stripe regions 32 by the same width as that of the irradiation region 34. Each stripe region 32 is divided into a plurality of unit inspection regions 33 by the size (width and length) being the same as that of the irradiation region 34. First, the XY stage 105 is moved to make an adjustment so that the irradiation region 34, which can be irradiated with one-shot irradiation of the multi-beams 20, may be located outside (in this case, further left than the left end) of the first stripe region 32, being towards the outside by the size of one unit inspection region 33, and then, a scanning operation is started. According to the first embodiment, by continuously moving the XY stage 105 in the −x direction, the irradiation region 34 is relatively moved in the x direction continuously. By this operation, a plurality of unit inspection regions 33 aligned in the x direction are scanned in order. When scanning the first stripe region 32, the XY stage 105 is moved in the −x direction, for example, so that the scanning operation advances in the x direction relatively. After completing the irradiation of the multi-beams for inspection of the first stripe region 32, the stage position is moved in the −y direction to make an adjustment such that the irradiation region 34 is located, in the y direction relatively, at a position further right than the right end of the second stripe region 32. Next, by moving the XY stage 105 in the x direction, for example, multi-beam irradiation advances in the −x direction. That is, scanning is performed while alternately changing the direction, such as performing the multi-beam irradiation in the x direction in the third stripe region 32, and in the −x direction in the fourth stripe region 32, and thus, the inspection time can be reduced. However, the scanning operation is not limited to the case of performing scanning while alternately changing the direction, and it is also preferable to perform scanning in the same direction when writing each stripe region 32. The multi-secondary electrons 300 being a flux of secondary electrons corresponding to a plurality of beams (primary electron beams) whose number is equal to the number of the holes 22 at the maximum are detected simultaneously by using the multi-beams 20 which were formed by being passed through each of the holes 22 of the shaping aperture array substrate 203.

Figure 5:
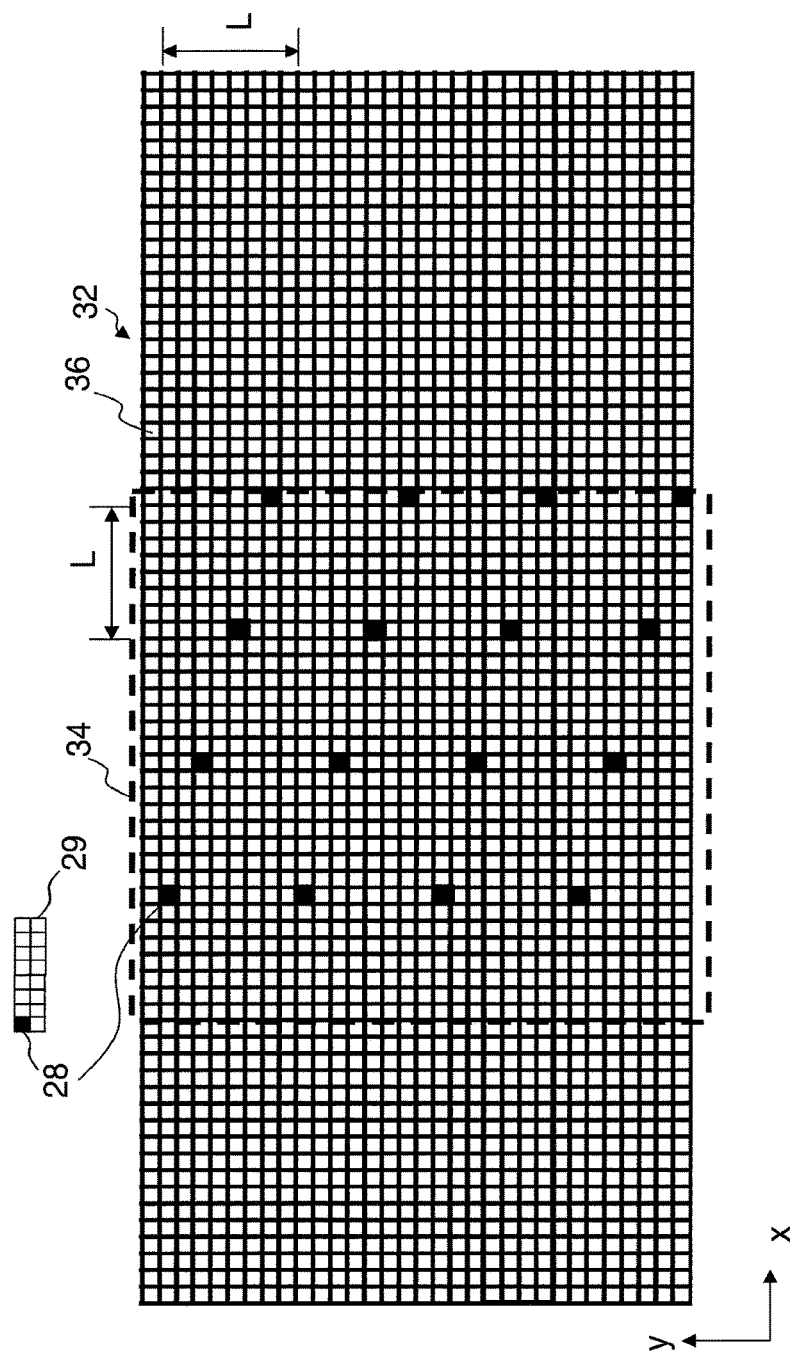
FIG. 5 shows an example of an irradiation region of multi-beams and a measurement pixel according to the first embodiment.

FIG. 5 shows an example of an irradiation region of multi-beams and a measurement pixel according to the first embodiment. In FIG. 5, each stripe region 32 is divided into a plurality of mesh regions by the beam size of the multi-beams, for example. Each mesh region serves as a measurement pixel 36 (unit irradiation region). In the irradiation region 34, there are shown a plurality of measurement pixels 28 (irradiation positions of beams of one shot) which can be irradiated with one irradiation of the multi-beams 20. In other words, a pitch L, in the x and y directions, between adjacent measurement pixels 28 serves as the pitch between beams of the multi-beams. In the example of FIG. 5, one grid 29 is a rectangular region, including one of four adjacent measurement pixels 28 as one of the four corners of the rectangular region and extending L in the x direction and L/M in the −y direction, in a region extending L in the x and y directions (L×L) starting from the one measurement pixel 28. In the case of FIG. 5, each grid 29 (individual beam scan region) is composed of 8×2 pixels.

Figure 6:
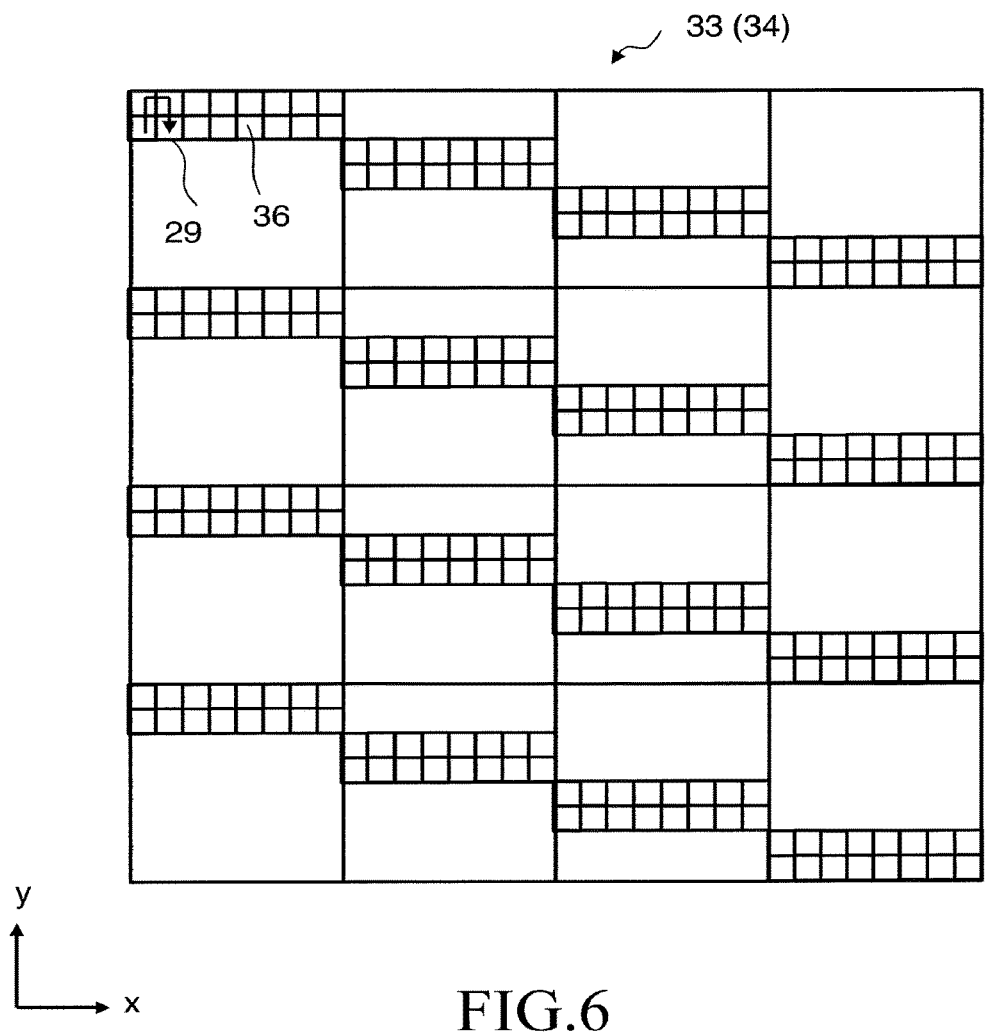
FIG. 6 is a conceptual diagram describing an example of details of a scanning operation according to the first embodiment.

FIG. 6 is a conceptual diagram describing an example of details of a scanning operation according to the first embodiment. FIG. 6 shows an example of scanning a certain unit inspection region 33 (irradiation region 34). In one irradiation region 34, there are arranged m×n(L/M) grids 29 in the x and y directions (two-dimensionally). In such a state, while the XY stage 105 continuously moves in the −x direction (predetermined direction), the electron beam column 102 (an example of a column) scans the substrate 101 by irradiating the substrate 101 with the multi-beams 20, composed of a plurality of electron beams (first electron beam) in an array of a plurality of beam rows in each of which beams are arranged in a straight line at the same pitch, such that the beam irradiation regions of the multi-beams 20 do not overlap with each other in the direction parallel to the movement direction (−x direction) of the XY stage 105. Specifically, scanning (scanning operation) is performed in the unit inspection region 33 concerned while the irradiation region 34 of the multi-beams 20 relatively moves in the x direction continuously as the XY stage 105 continuously moves in the −x direction. The example of FIG. 6 shows the state where one unit inspection region 33 and the irradiation region 34 of the multi-beams 20 overlap with each other so as to be coincident with each other. Each beam of the multi-beams 20 takes charge of one of grids 29 being different from each other. At the time of each shot, each beam irradiates one measurement pixel 36 in the grid 29 concerned, that is, each of the measurement pixels 36 irradiated by the multi-beams 20 is equivalent to the same position in each grid 29. In the case of FIG. 6, the first shot of each beam irradiates the first measurement pixel 36 from the left in the bottom row in the grid 29 concerned. Then, the beam deflection position is shifted in the y direction by the size of one measurement pixel 36 by collectively deflecting the entire multi-beams 20 by the sub deflector 209, and the second shot irradiates the first measurement pixel 36 from the left in the second row from the bottom in the grid 29 concerned. Then, the beam deflection position is shifted in the x direction by the size of one measurement pixel 36 by collectively deflecting the entire multi-beams 20 by the sub deflector 209, and the third shot irradiates the second measurement pixel 36 from the left in the second row from the bottom in the grid 29 concerned. Then, the beam deflection position is shifted in the −y direction by the size of one measurement pixel 36 by collectively deflecting the entire multi-beams 20 by the sub deflector 209, and the fourth shot irradiates the second measurement pixel 36 from the left in the bottom row in the grid 29 concerned. By repeating this operation, all the measurement pixels 36 in one grid 29 are irradiated in order with one beam. The multi-secondary electrons 300 being a flux of secondary electrons corresponding to a plurality of shots whose maximum number is the same as the number of a plurality of holes 22 are detected at a time by using the multi-beams which were formed by being passed through each of the holes 22 of the shaping aperture array substrate 203. The main deflector 208 deflects (tracking operation) the multi-beams 20 so as to follow the movement of the XY stage 105 so that the deflection position may not be shifted due to the movement of the XY stage 105 until the multi-beams 20 scan all the measurement pixels 36 in the grid 29 concerned. When the multi-beams 20 scan all the measurement pixels 36 in the grid 29 concerned, the main deflector 208 performs tracking reset, and shifts the deflection position of the entire multi-beams 20 so that the position of the pixel 36 for the first shot in the next grid 29 adjacent in the x direction may be irradiated with each beam. Then, similarly, the scanning operation is proceeded.

Although here description is performed for each shot such as, the first shot, the second shot, and so on, the multi-beams 20 may perform a raster scan operation of moving the deflection position while continuing to irradiate without turning on/off the beam for each pixel 36.

As described above, each beam individually scans one corresponding grid 29. Due to a shot of the multi-beams 20, a secondary electron is emitted upward from the irradiated measurement pixel 36, at each time of the shot. Thus, the multi-detector 222 detects secondary electrons emitted from the substrate 101 due to irradiation of the multi-beams 20 on the substrate 101. The multi-detector 222 detects, for each measurement pixel 36 (or each grid 29), multi-secondary electrons 300 emitted upward from each irradiated measurement pixel 36.

By performing scanning using the multi-beams 20 as described above, the scanning operation (measurement) can be performed at a higher speed than scanning by a single beam.

Figure 7:
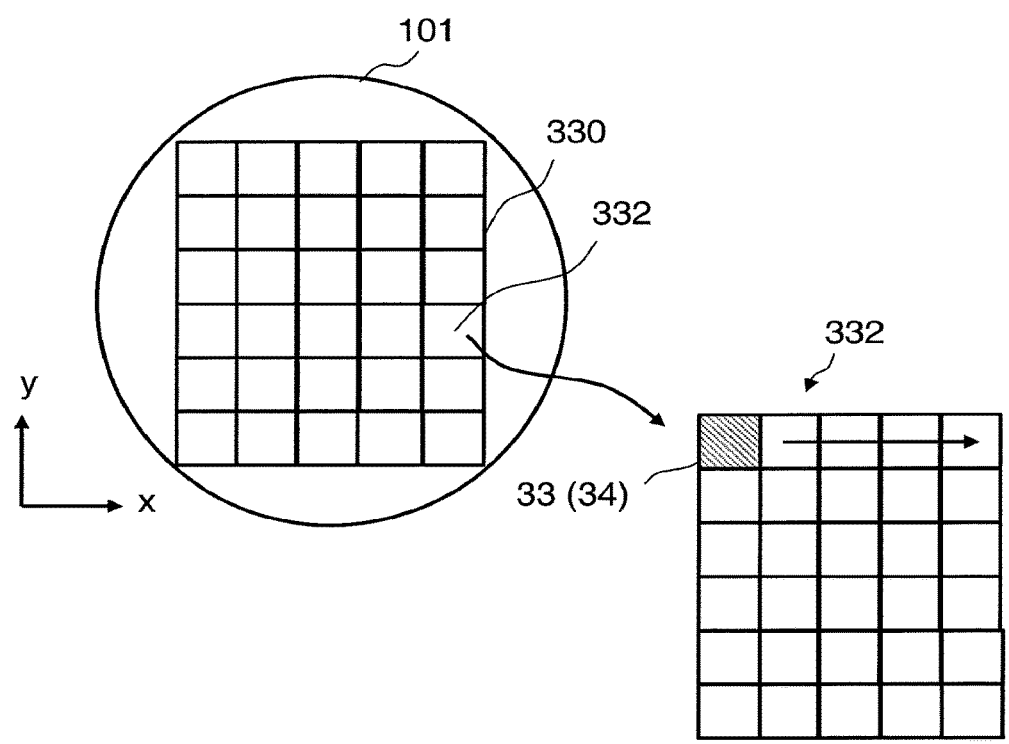
FIG. 7 is a conceptual diagram illustrating another example of a scanning operation according to the first embodiment.

FIG. 7 is a conceptual diagram illustrating another example of a scanning operation according to the first embodiment. As shown in FIG. 7, a plurality of chips 332 (die) each having predetermined width and length are formed, for example, in an array in the x and y directions in an inspection region 330 of the substrate 101. Here, preferably, the substrate 101 to be inspected can be a semiconductor substrate (for example, wafer). Each chip 332 having a size of 30 mm×25 mm, for example, is formed on the substrate 101. Pattern inspection is performed for each chip 332. The region of each chip 332 is virtually divided into a plurality of unit inspection regions 33 by the same size (width and length in the x and y directions) as that of the irradiation region 34 which can be irradiated with one-shot irradiation of the entire multi-beams 20, for example. First, the XY stage 105 is moved to make an adjustment so that the irradiation region 34, which can be irradiated with one-shot irradiation of the multi-beams 20, may be located outside (−x direction side) of the unit inspection region 33 at one (upper left end, for example) of the four corners of the first chip 332, being towards the outside by the size of one unit inspection region 33, and then, a scanning operation is started. The contents of the scanning operation are the same as those described with reference to FIGS. 5 and 6. As described above, according to the first embodiment, by continuously moving the XY stage 105 in the −x direction, the irradiation region 34 is relatively moved in the x direction continuously in order to scan each unit inspection regions 33 with the multi-beams 20. After finishing scanning all the unit inspection regions 33 aligned in the x direction in the same y direction position row, the stage position is moved in the −y direction to similarly scan the unit inspection regions 33 aligned along the x direction in a next row in the rows arrayed in the y direction with the multi-beams 20. While repeating this operation, after finishing scanning the region of one chip 332, the XY stage 105 is moved to similarly scan the unit inspection region 33 at one (upper left end, for example) of the four corners of the next chip 332. By repeating this operation, scanning is performed on all the chips 332.

According to the first embodiment, for example, when performing scanning per stripe region 32, it is sufficient to continuously move (for example, in the −x direction) the XY stage 105 by the longitudinal length (for example, x direction) of the stripe region 32 and a length corresponding to the length of two irradiation regions 34 before and after the stripe region 32 concerned. For example, when performing scanning per chip 332, it is sufficient to continuously move (for example, in the −x direction) the XY stage 105 by the length in the x direction of the chip 332 and a length corresponding to the length of two irradiation regions 34 before and after the chip 332 concerned.

Figure 8A:
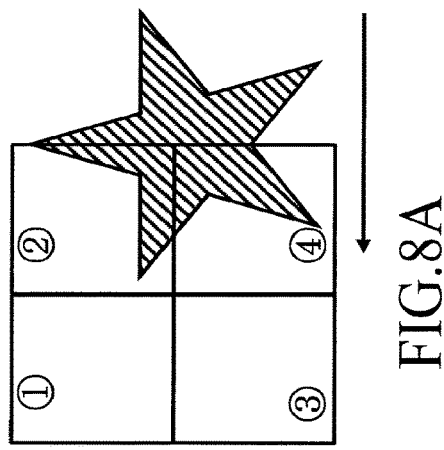
FIGS. 8A to 8C illustrate a scanning operation in a comparative example to the first embodiment.
Figure 8B:
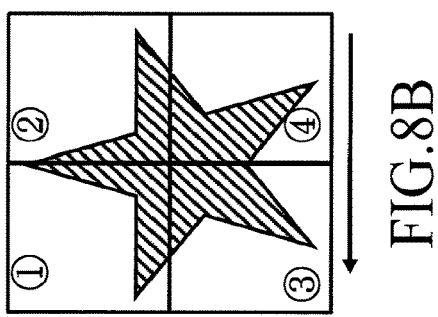
Figure 8C:
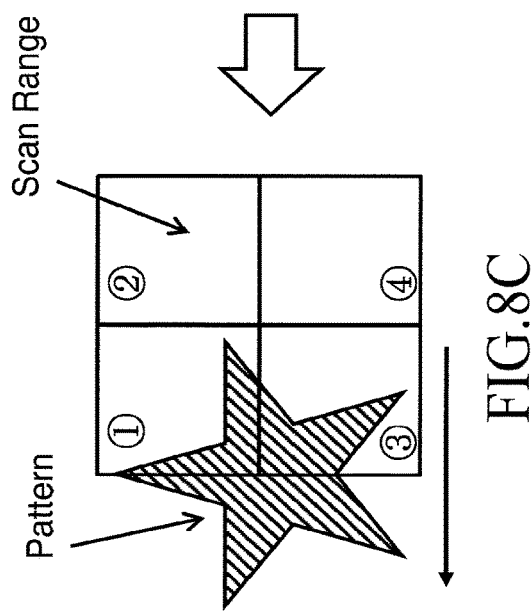

FIGS. 8A to 8C illustrate a scanning operation in a comparative example to the first embodiment.

Figure 9A:
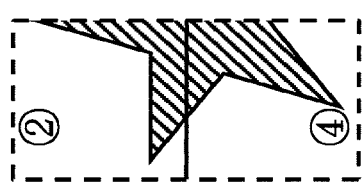
FIGS. 9A to 9C illustrate images obtained by a scanning operation in a comparative example to the first embodiment.
Figure 9B:
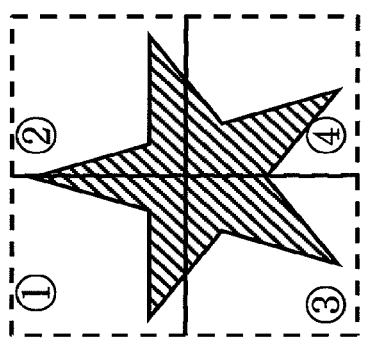
Figure 9C:
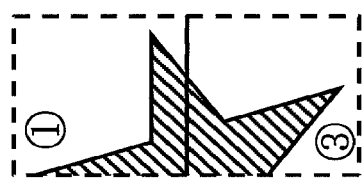

FIGS. 9A to 9C illustrate images obtained by a scanning operation in a comparative example to the first embodiment.

Figure 10:
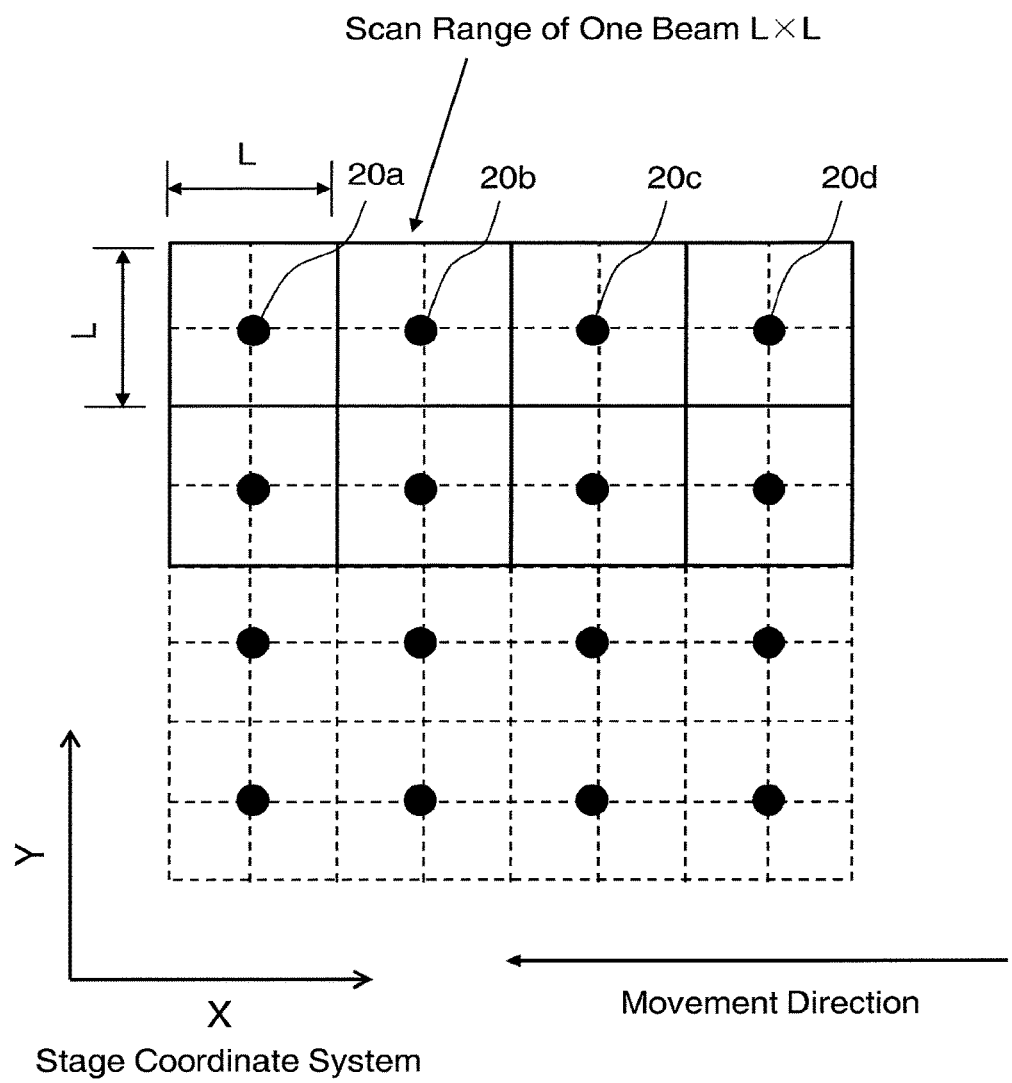
FIG. 10 shows an arrangement state of multi-beams in a comparative example to the first embodiment.

FIG. 10 shows an arrangement state of multi-beams in a comparative example to the first embodiment. As shown in FIG. 10, in the comparative example to the first embodiment, it is assumed that a scanning operation is performed using multi-beams in which a plurality of beams are arranged in a matrix (x and y directions). That is, it is assumed that each beam is arranged at a predetermined pitch in a row in the x direction, and the plurality of beams aligned in the row in the x direction are arrayed without shifting in the y direction. Such rows are arrayed in the y direction. The example of FIG. 10 shows the multi-beams 20 composed of 4×4 beams. When arranged in the x and y directions at a pitch L, the individual beam scan range of each beam is an L×L square region surrounded by four adjacent beams. FIG. 8A shows a range of 2×2 in the x and y directions to be scanned by beams 1 to 4 in the multi-beams 20 of 4×4 shown in FIG. 10. In FIG. 8A, the beams 1 and 2 overlap with each other in the x direction, and the beams 3 and 4 overlap with each other in the x direction. By continuously moving the XY stage 105 in the −x direction, a pattern is sent to the scan range of the beams 2 and 4 as shown in FIG. 8A. Then, the left side half of the pattern is scanned by the beams 2 and 4, and the first image of the left side half of the pattern is obtained as shown in FIG. 9A. Then, along with the movement of the XY stage 105, as shown in FIG. 8B, the right half of the pattern overlaps with the scanning range of the beams 2 and 4, and the left half of the pattern overlaps with the scanning range of beams 1 and 3. Then, the right half of the pattern is scanned by the beams 2 and 4, and the left half of the pattern whose image has already been obtained is again scanned by the beams 1 and 3. Thereby, as shown in FIG. 9B, the second image of the left half of the pattern and the first image of the right half of the pattern are obtained. Thereafter, along with further movement of the XY stage 105, as shown in FIG. 8C, the right half of the pattern overlaps with the scan range of the beams 1 and 3. Then, the right half of the pattern is scanned by the beams 1 and 3, and the second image of the right half of the pattern is obtained as shown in FIG. 9C. As described above, when the beams 20a to 20d overlap with each other or the scan ranges overlap with each other in the movement direction of the XY stage 105, images of the pattern are obtained in an overlapping manner. Therefore, time is spent on acquiring an unnecessary image, and even if the XY stage 105 is continuously moved, the effect of improving the throughput is not efficient. Therefore, according to the first embodiment, it is aimed to improve the throughput by shifting the beam arrangement position.

Figure 11:
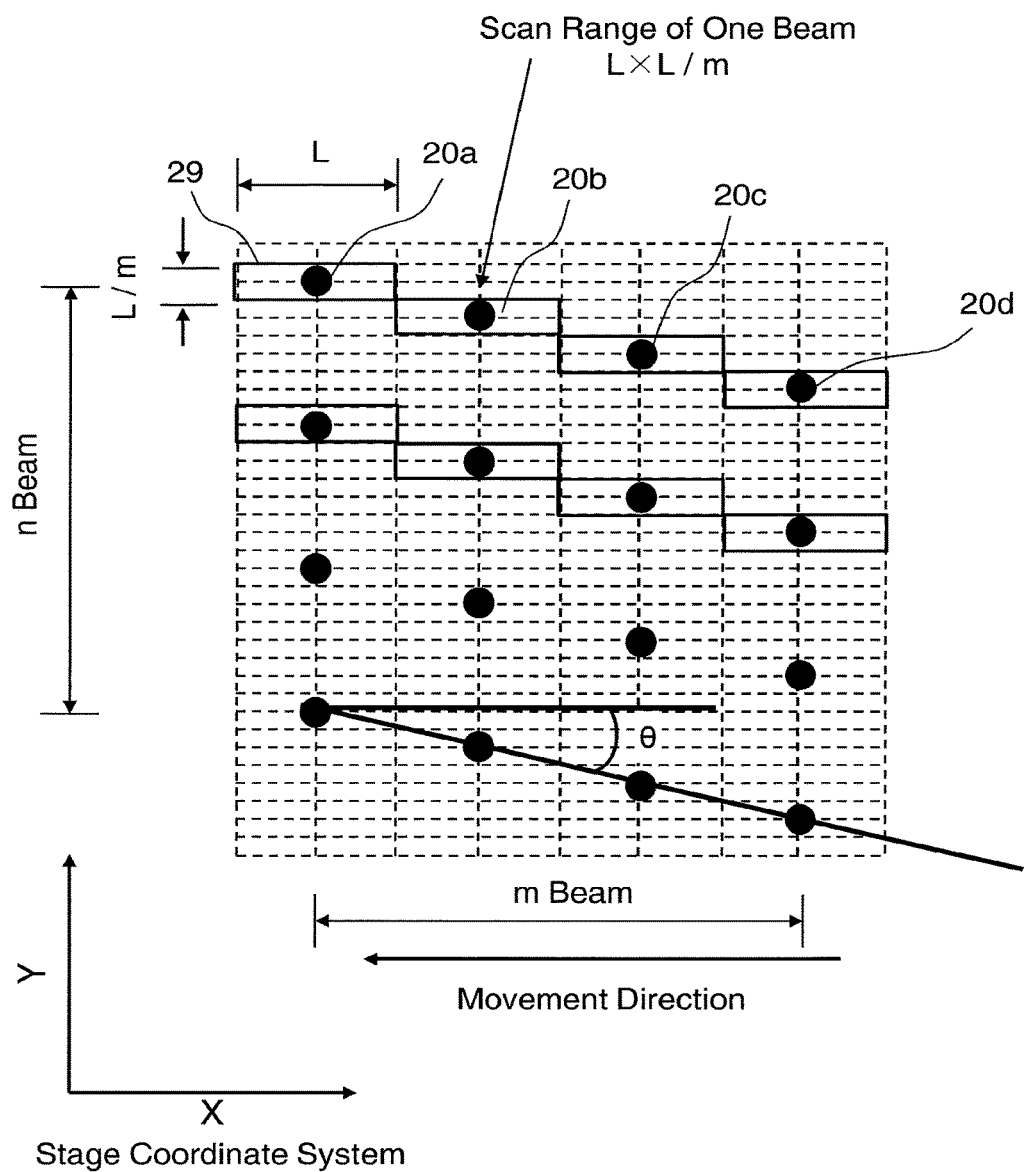
FIG. 11 illustrates an arrangement state of multi-beams according to the first embodiment.

FIG. 11 illustrates an arrangement state of multi-beams according to the first embodiment. The example of FIG. 11 shows the multi-beams 20 composed of 4×4 beams arranged in the x and y directions at a pitch L. However, according to the first embodiment, each of the beams 20a to 20d aligned in the x direction in each row, where such rows are arrayed in the y direction, is shifted by L/m (L/4 in the case of FIG. 11) in the −y direction in order. In other words, when arranging m×n beams in the x and y directions, each of the beams 20a to 20d aligned in the x direction in each row, where such rows are arrayed in the y direction, is arranged along the straight line which is shifted by the angle θ(=tan$^{-1}$ (1/m)) in a clockwise direction. According to the first embodiment, a plurality of holes 22 are two-dimensionally formed such that they do not overlap with each other in the movement direction (−x direction) of the XY stage 105 moving continuously, and they are arranged at the same pitch in a plurality of straight lines arrayed in parallel to each other at the same interval in the shaping aperture array substrate 203. Then, by irradiating the whole of a plurality of holes 22 of the shaping aperture array substrate 203 with the electron beam 200 (second electron beam) so as to make portions of the electron beam 200 individually pass through a corresponding one of a plurality of holes 22, it is possible to form the multi-beams 20 which do not overlap with each other in the movement direction of the XY stage 105. Thereby, the scan range (grid 29) of one beam can be a rectangular region of L×L/m width and length in the x and y directions. Thus, with respect to the size (dimension) of the deflection region (scan range: grid 29) for deflecting each of the multi-beams 20, the width in the movement direction (−x direction) of the XY stage 105 differs from the length in the direction (y direction) orthogonal to the movement direction of XY stage 105. It is possible to shorten the length along the direction (y direction) orthogonal to the movement direction of the XY stage 105. Thus, the electron beam column 101 scans the substrate 101 by deflecting the multi-beams 20 such that the scan range in the x direction differs from the scan range in the y direction.

Figure 12:
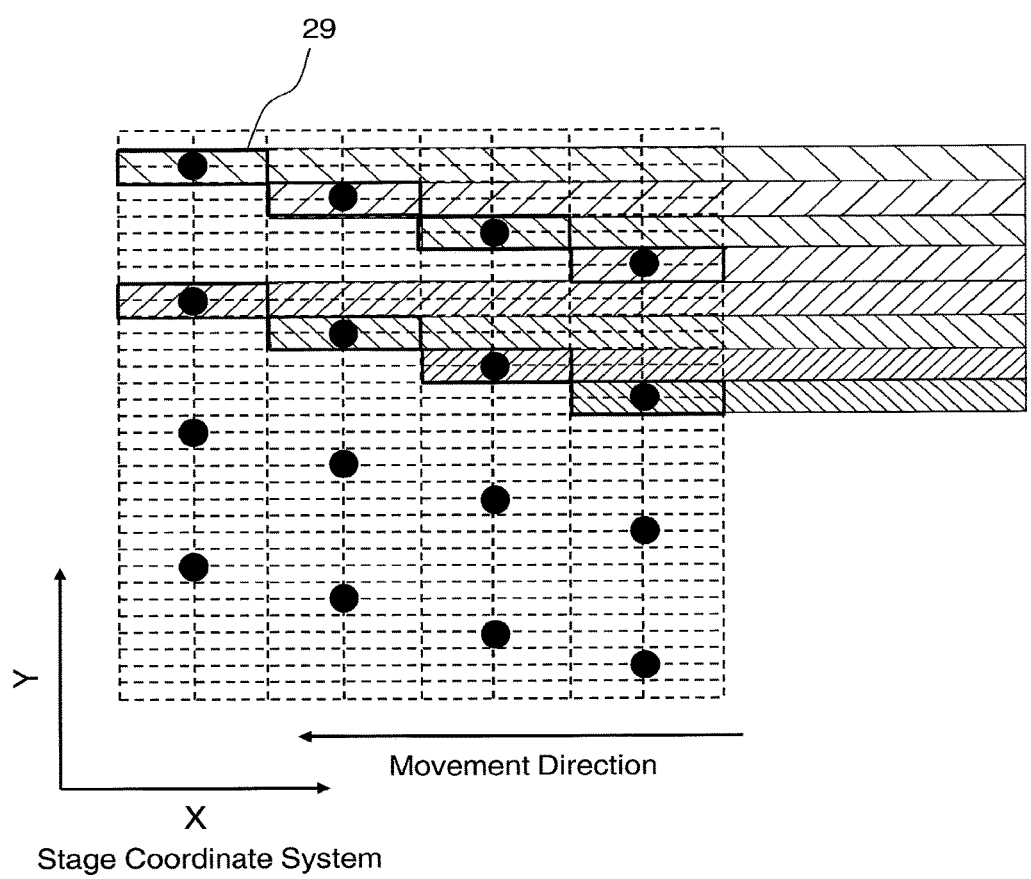
FIG. 12 is another conceptual diagram illustrating details of a scanning operation according to the first embodiment.

FIG. 12 is another conceptual diagram illustrating details of a scanning operation according to the first embodiment. Scanning (scanning operation) is performed while the irradiation region 34 of the multi-beams 20 relatively moves in the x direction continuously as the XY stage 105 continuously moves in the −x direction. As shown in FIG. 12, the beams 20a to 20d aligned in the x direction in each row, where such rows are arrayed in the y direction, are arranged not to overlap with each other in the movement direction (−x direction) of the XY stage 105, and, also, the scan ranges (grids 29) of the beams 20a to 20d are arranged not to overlap with each other in the movement direction (−x direction) of the XY stage 105. Therefore, when the XY stage 105 is moved continuously, it is possible to avoid scanning the same region with a plurality of different beams.

Figure 13A:
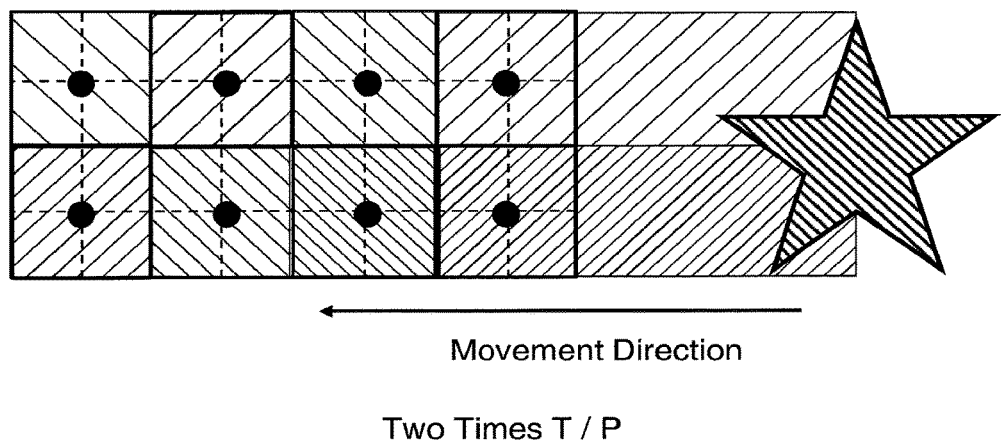
FIGS. 13A and 13B show comparison between throughputs of the first embodiment and a comparative example.
Figure 13B:
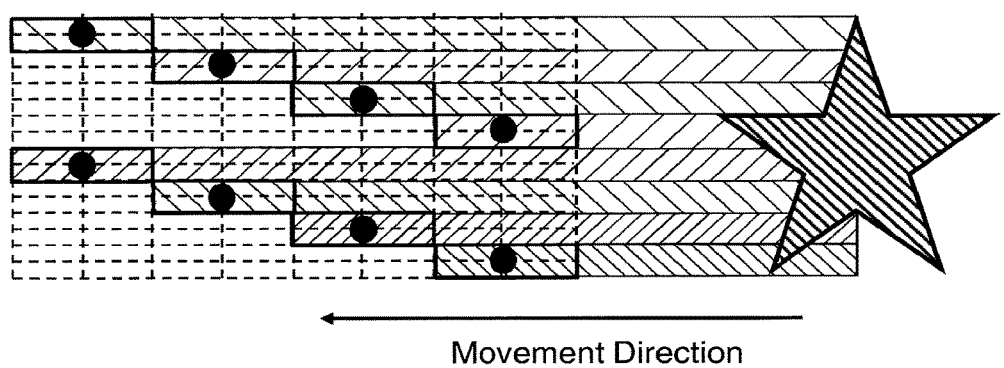

FIGS. 13A and 13B show comparison between throughputs of the first embodiment and a comparative example. FIG. 13A shows, as a comparative example, the case where 4×2 beams are arranged in a matrix (x and y directions). The four beams aligned in the x direction in each row, where such rows are arrayed in the y direction, perform scanning in a mutually overlapping manner, eventually, which is the same as simultaneous scanning of different regions with beams in two rows arrayed in the y direction. Therefore, twice the throughput can be obtained compared to scanning with a single beam. In contrast, in FIG. 13B, as the first embodiment, the four beams aligned in the x direction in each row, where such rows are arrayed in the y direction, are shifted in order in the −y direction so that the scan ranges (grids 29) may not overlap with each other, which is the same as simultaneous scanning of different regions with beams in eight rows arrayed in the y direction. Therefore, eight times the throughput can be obtained compared to scanning with a single beam.

As described above, using the multi-beams 20 of a plurality of electron beams which do not overlap with each other in the movement direction (−x direction) of the XY stage 105 moving continuously, the electron optical image acquisition mechanism 150 scans the inspection substrate 101 on which a figure pattern is formed, and detects the multi-secondary electrons 300 emitted from the inspection substrate 101 due to irradiation of the multi-beams 20 on the inspection substrate 101. The method for scanning and the method for detecting the multi-secondary electrons 300 are what has been described above. Detected data on a secondary electron from each measurement pixel 36 detected by the multi-detector 222 is output to the detection circuit 106 in order of measurement. In the detection circuit 106, the detected data in analog form is converted into digital data by an A-D converter (not shown), and stored in the chip pattern memory 123. Then, at the stage when detected data for one stripe region 32 (or chip 332) has been accumulated, the accumulated data is transmitted as stripe pattern data (or chip pattern data) to the comparison circuit 108, with information on each position from the position circuit 107.

On the other hand, a reference image is formed (generated) in parallel or in tandem with the step of multi-beam scanning and secondary electron detecting.

In a reference image generation step, if the substrate 101 is a semiconductor substrate, a reference image generation unit, such as the development circuit 111 and the reference circuit 112, generates a reference image of a region corresponding to a measured image (electron optical image) of the inspection unit region 33 configured by a plurality of pixels 36, based on exposure image data defining an exposure image on the substrate used when a mask pattern of an exposure mask is exposed and transferred onto the semiconductor substrate. Instead of the exposure image data, writing data (design data) may be used which is a base for forming an exposure mask to expose and transfer a plurality of figure patterns onto the substrate 101. If the substrate 101 is an exposure mask, the reference image generation unit, such as the development circuit 111 and the reference circuit 112, generates a reference image of a region corresponding to a measured image (electron optical image) of the inspection unit region 33 configured by a plurality of pixels 36, based on writing data (design data) which is a base for forming a plurality of figure patterns on the substrate 101. An electron optical image may be generated as an image whose resolution is lower than that of an image using the pixel 36 as one pixel and in which a grid 29 or a rectangular region where m grids 29 are aligned in the y direction is treated as one pixel. In such a case, a reference image can be similarly generated as an image of the unit inspection region 33, whose resolution is lower than that of an image using the pixel 36 as one pixel and in which a grid 29 or a rectangular region where m grids 29 are aligned in the y direction is treated as one pixel. In the case where the grid 29 or a rectangular region in which m grids 29 are aligned in the y direction is one pixel, the pattern occupancy in the grid 29 or in the rectangular region in which m grids 29 are aligned in the y direction can be a gray scale value.

Specifically, it operates as follows: First, the development circuit 111 reads writing data (or exposure image data) from the storage device 109 through the control computer 110, converts each figure pattern of each inspection unit region 33 defined in the read writing data (or exposure image data) into image data of binary or multiple values, and transmits this image data to the reference circuit 112.

Here, basics of figures defined by writing data (or exposure image data) are, for example, rectangles or triangles. For example, there is stored figure data defining the shape, size, position, and the like of each pattern figure by using information, such as coordinates (x, y) of the reference position of the figure, lengths of sides of the figure, and a figure code serving as an identifier for identifying the figure type such as a rectangle, a triangle and the like.

When writing data (or exposure image data) used as figure data is input to the development circuit 111, the data is developed into data of each figure. Then, figure codes, figure dimensions and the like indicating figure shapes of the figure data are interpreted. Then, the development circuit 111 develops design image data of binary or multiple values, as patterns to be arranged in squares in units of grids of predetermined quantization dimensions, and outputs the developed data. In other words, the development circuit 111 reads design data, calculates an occupancy rate of a figure in a design pattern for each square obtained by virtually dividing an inspection region into squares in units of predetermined dimensions, and outputs n-bit occupancy rate data. For example, it is preferable that one square is set as one pixel. Assuming that one pixel has a resolution of $1/2^8 (=1/256)$, a small region of $1/256$ is allocated to the figure arranged in a pixel such that the allocated region corresponds to the figure so as to calculate the occupancy rate in the pixel. Then, the calculated rate is output as 8-bit occupancy rate data to the reference circuit 112. The size of the square should preferably be the same as that of the measurement pixel 36. In the case where the grid 29 or a rectangular region in which m grids 29 are aligned in the y direction is one pixel, the square size should preferably be the same as that of the grid 29 or the rectangular region in which m grids 29 are aligned in the y direction.

Next, the reference circuit 112 performs appropriate filter processing on design image data being transmitted figure image data. Since the measured target data as an optical image obtained from the detection circuit 106 is in the state affected by the filtering by the electron optical system, in other words, in the analog state continuously changing, it becomes possible to match/fit the design image data with the measured target data by also applying the filtering to the design image data being image data on the design side whose image intensity (gray value) is represented by digital values. In this manner, a design image (reference image) to be compared with a measured image (optical image) of the inspection unit region 33 is generated. The generated image data of the reference image is input into the comparison circuit 108 to be stored in the memory.

Figure 14:
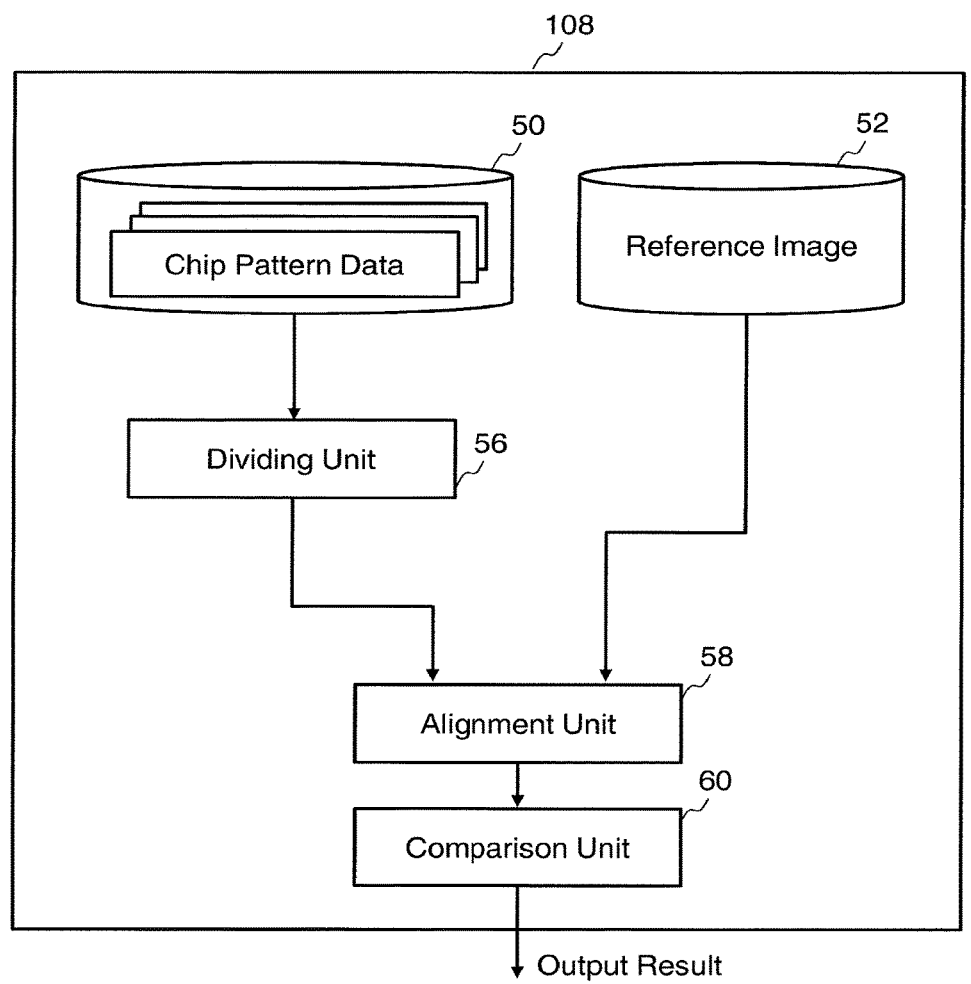
FIG. 14 shows an internal configuration of a comparison circuit according to the first embodiment.

FIG. 14 shows an internal configuration of a comparison circuit according to the first embodiment. In FIG. 14, storage devices 50 and 52, such as magnetic disk drives, a dividing unit 56, an alignment unit 58, and a comparison unit 60 are arranged in the comparison circuit 108. Each of the "units" such as the dividing unit 56, the alignment unit 58, and the comparison unit 60 includes a processing circuitry. As the processing circuitry, for example, an electric circuit, computer, processor, circuit board, quantum circuit, or semiconductor device may be used. Each of the "units" may use a common processing circuitry (same processing circuitry), or different processing circuitries (separate processing circuitries). Input data required in the dividing unit 56, the alignment unit 58, and the comparison unit 60, and calculated results are stored in a memory (not shown) each time.

The transmitted stripe pattern data (or chip pattern data) is temporarily stored in the storage device 50, with information indicating each position from the position circuit 107. Similarly, reference image data is temporarily stored in the storage device 52, with information indicating each design position.

Next, the dividing unit 56 divides the stripe pattern data (or chip pattern data) for each inspection unit region 33, and generates a plurality of frame images.

Next, the alignment unit 58 provides positioning between a frame image (measured target image) and a reference image, for each sub-pixel unit smaller than the pixel 36. For example, positioning may be performed by a least-square method.

The comparison unit 60 compares, for each pixel 36, the frame image concerned and the reference image. The comparison unit 60 compares both the images for each pixel 36, based on predetermined determination conditions in order to determine whether there is a defect such as a shape defect. For example, if a gray scale value difference of each pixel 36 is larger than a determination threshold Th, it is determined that there is a defect. Then, the comparison result is output, and specifically, output to the storage device 109, monitor 117, or memory 118, or alternatively, output from the printer 119. In the case of an image whose pixel is the grid 29 or a rectangular region where m grids 29 are aligned in the y direction, the pixel 36 should be read as the grid 29 or the rectangular region where m grids 29 are aligned in the y direction.

As described above, according to the first embodiment, even when the XY stage 105 is moved continuously in performing a pattern inspection using the multi-beams 20 in which beams are aligned at the same pitch in a straight line in each of a plurality of arrayed rows, it is possible not to transmit the same small region on the substrate 101 to the scan ranges of a plurality of beams. Therefore, the throughput can be improved in the pattern inspection using multi-beams where there are a plurality of arrayed rows in each of which beams are aligned at the same pitch in a straight line.

Although, in the examples described above, the scanning range of each beam is L wide in the x direction and L/m long in the y direction in order not to overlap with scanning ranges of other beams, it is not limited thereto. For example, the scanning range Scany in the y direction may be defined as $L/m \leq Scany \leq 2L/m$, which causes a partial overlap in the y direction. Therefore, the scanning may be performed such that the center of each of irradiation regions irradiated with the multi-beams does not overlap with the other irradiation regions in a direction parallel to a movement direction of the stage. Due to this, although the throughput decreases, it becomes possible to eliminate regions that are not scanned due to errors or the like. Moreover, by narrowing the tracking range in the x direction, the scanning range Scanx in the x direction can be defined as $Scanx \leq L$.

Second Embodiment

In the first embodiment, it is structured to form multi-beams at positions where the positions themselves do not overlap with each other in the movement direction of XY stage 105. However, it is not limited thereto. The structure of the inspection apparatus in a second embodiment is the same as that of FIG. 1. The contents of the present embodiment are the same as those of the first embodiment except for what is specifically described below.

Figure 15:
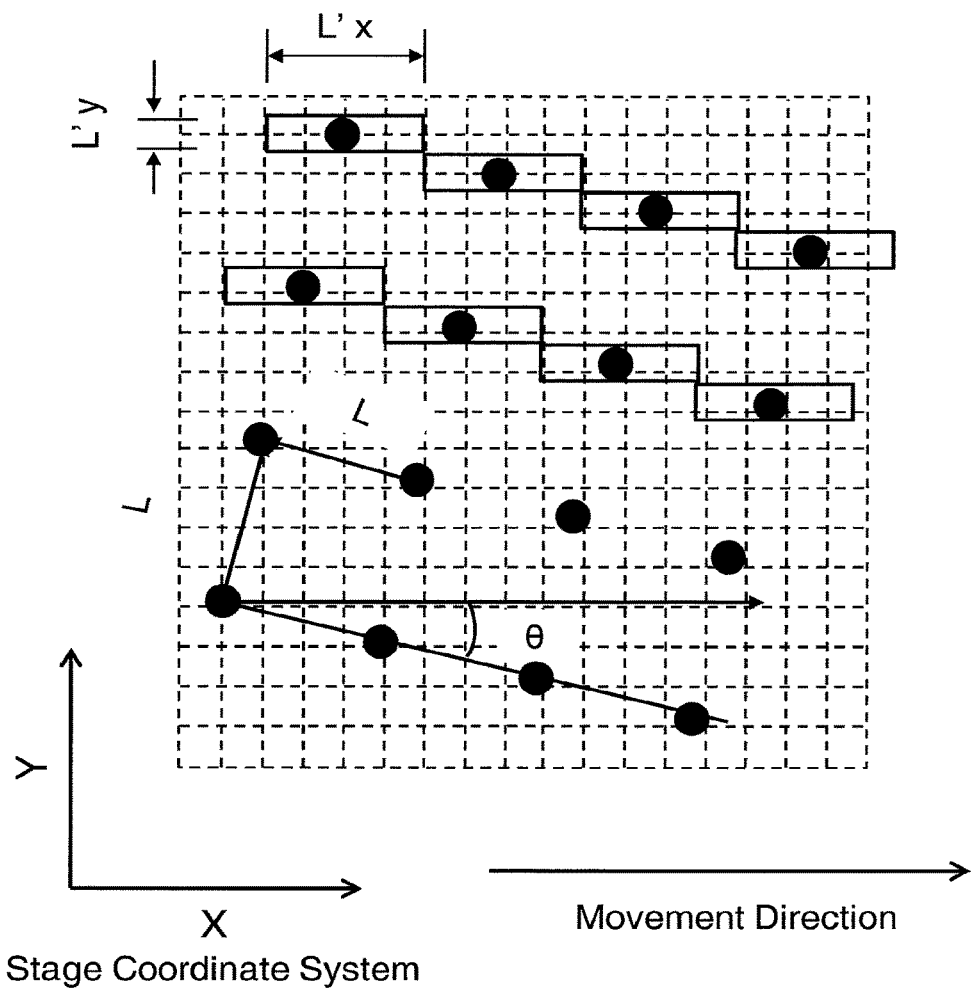
FIG. 15 shows an example of a beam arrangement on an inspection substrate according to a second embodiment.

FIG. 15 shows an example of a beam arrangement on an inspection substrate according to the second embodiment. In the second embodiment, a plurality of beams aligned in the x direction in each of rows arrayed in the y direction are not shifted in the y direction on the shaping aperture array substrate 203. That is, each row in which m beams are aligned along the x direction is arrayed in the y direction to form n rows. In other words, the multi-beams 20 are arranged in a matrix in the x and y directions. However, if this state remains unchanged, as described in the above comparative example, since the beams aligned in the x direction in each row overlap with each other in the movement direction (−x direction) of the XY stage 105, the same region is scanned in an overlapping manner by the beams aligned in the x direction. Therefore, according to the second embodiment, as shown in FIG. 15, before irradiating the substrate 101 with the multi-beams 20 of m×n beams, the image of the multi-beams 20 (or "entire multi-beams 20") is rotated clockwise by an angle $\theta (=\tan^{-1}(1/m))$, for example. In the second embodiment, images of the multi-beams 20 are rotated by the electron optical system so that each beam in the multi-beams 20 may not overlap with each other in the movement direction (−x direction) of the XY stage 105 moving continuously. Specifically, the rotation angle θ for rotating the image of the multi-beams 20 can be obtained by adjusting a current value which the lens control circuit 124 flows to excite the electron optical system such as the reducing lens 205 and the objective lens 207. Alternatively, an electron optical system such as an electrostatic lens or the like (not shown in FIG. 1) that affects the rotation of the image may be additionally arranged in the electron optical image acquisition mechanism 150, and the rotation angle θ for rotating the image of the multi-beams 20 may be obtained by adjusting the potential to be applied to the electrostatic lens. Alternatively, the shaping aperture array substrate 203 itself may be rotated.

By rotating the image of the multi-beams 20, the scanning range of each beam is affected by the change amount Δ due to rotation.

Figure 16A:
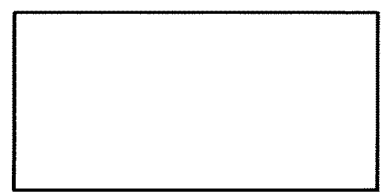
FIGS. 16A to 16D illustrate change amounts due to rotation according to the second embodiment.
Figure 16C:
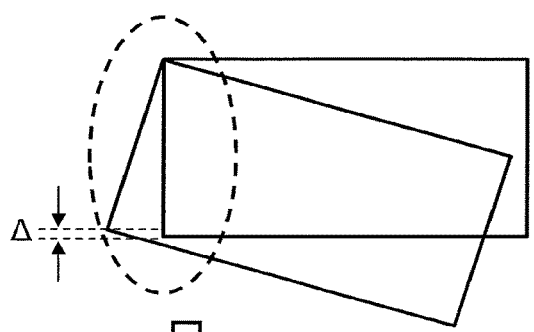
Figure 16B:
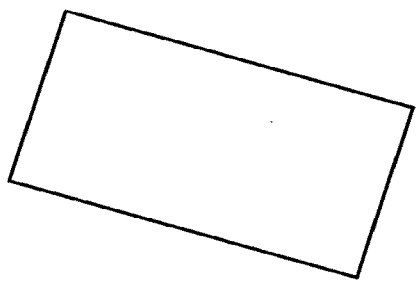
Figure 16D:
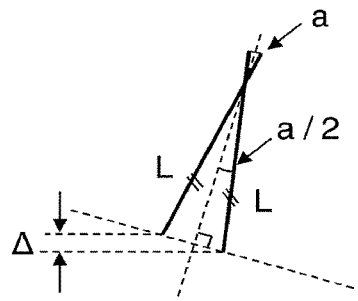

FIGS. 16A to 16D illustrate change amounts due to rotation according to the second embodiment. FIG. 16A shows the image of a scanning range of each beam in the case of not rotating the shaping aperture array substrate 203. FIG. 16B shows the image of a scanning range of each beam in the case of rotating the shaping aperture array substrate 203. When the scanning ranges of beams in the case of rotating and not rotating are overlapped with each other, it changes by the change amount Δ in the y direction as shown in FIG. 16C. When the change amount Δ is calculated using the triangle shown in FIG. 16C, Δ can be defined by $\Delta = 2L (\sin(\alpha/2))^2$ based on a relation as shown in FIG. 16D. The scanning range of each beam is obtained by using this change amount Δ. The scanning range (grid 29) according to the second embodiment is (L−Δ) wide in the x direction and (L−Δ)/m long in the y direction.

As described above, also in the case of performing scanning while the XY stage 105 is continuously moving in the state where the image of the multi-beams has been rotated, it is possible not to transmit the same small region on the substrate 101 to the scan ranges of a plurality of beams as well as the first embodiment. Therefore, the throughput can be improved in the pattern inspection using multi-beams where there are a plurality of arrayed rows in each of which beams are aligned at the same pitch in a straight line.

Similarly to the first embodiment, the scanning range Scany in the y direction may be defined as (L−Δ)/m≤Scany≤2 (L−Δ)/m, which causes a partial overlap in the y direction. Due to this, although the throughput decreases, it becomes possible to eliminate regions that are not scanned due to errors or the like. Moreover, by narrowing the tracking range in the x direction, the scanning range Scanx in the x direction can be defined as Scanx≤(L−Δ).

Third Embodiment

In the second embodiment, it is structured to rotate the position of the image of multi-beams on the substrate 101 with respect to the continuous movement direction of the XY stage 105. However, it is not limited thereto. The structure of the inspection apparatus in a third embodiment is the same as that of FIG. 1. The contents of the present embodiment are the same as those of the first or second embodiment except for what is specifically described below.

Figure 17:
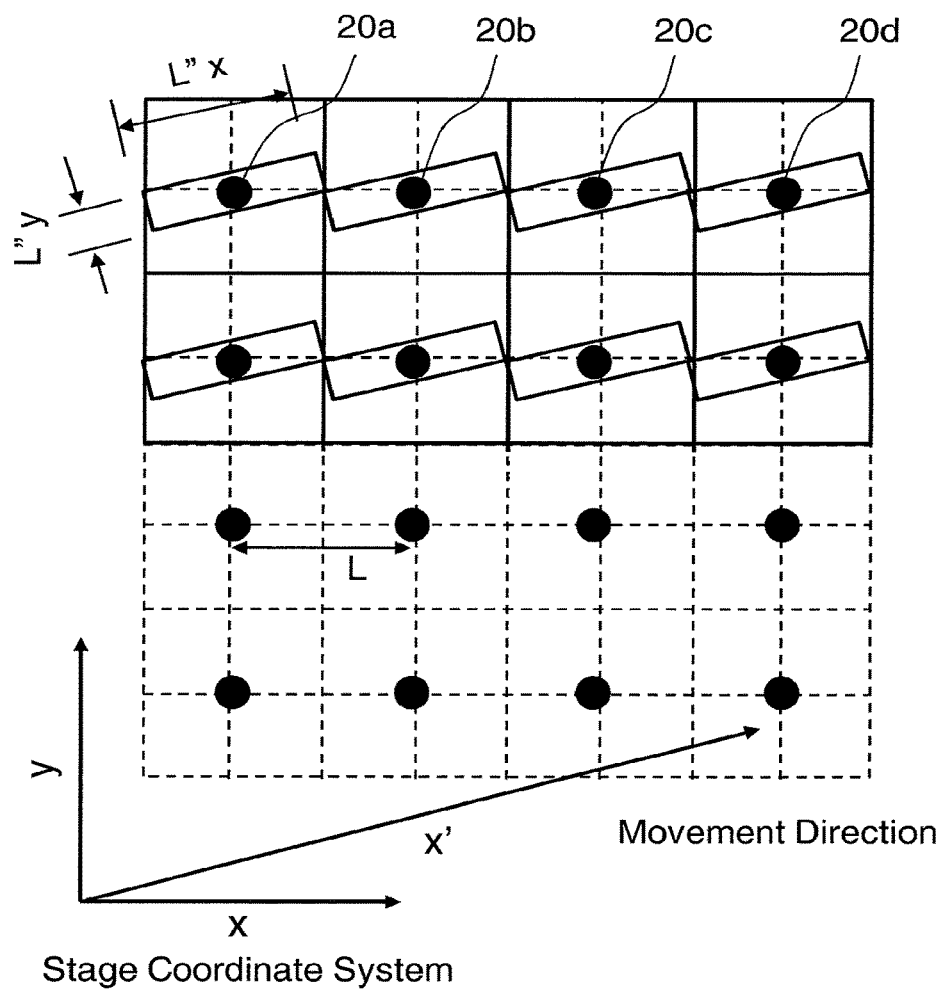
FIG. 17 shows an example of a beam arrangement on an inspection substrate according to a third embodiment.

FIG. 17 shows an example of a beam arrangement on an inspection substrate according to the third embodiment. In the third embodiment, instead of rotating the image of multi-beams, direction of continuous movement of the XY stage 105 is rotated counter-clockwise by the angle θ(=tan$^{-1}$(1/m)). Said differently, the multi-beams 20 are arranged in a matrix in the x and y directions. Then, while the surface of the substrate 101 is being scanned, the XY stage 105 continuously moves in the direction inclined so that the beams of the multi-beams 20 in a matrix in the x and y directions do not overlap with each other. According to the third embodiment, after the stage control circuit 114 converts the x-y coordinate system of stage driving into the x'-y' coordinate system which is rotated from the x-y coordinate system by the angle θ, the scanning operation is performed while the XY stage 105 is continuously moved in the x' direction. Similarly to the second embodiment, the scanning range (grid 29) in the third embodiment is (L−Δ) wide in the x' direction and (L−Δ)/m long in the y' direction.

As described above, also in the case of performing scanning while the XY stage 105 is continuously moving with its continuous movement direction having been rotated, it is possible not to transmit the same small region on the substrate 101 to the scan ranges of a plurality of beams as well as the first embodiment. Therefore, the throughput can be improved in the pattern inspection using multi-beams where there are a plurality of arrayed rows in each of which beams are aligned at the same pitch in a straight line.

Similarly to the second embodiment, the scanning range Scany in the y' direction may be defined as (L−Δ)/m≤Scany≤2(L−Δ)/m, which causes a partial overlap in the y' direction. Due to this, although the throughput decreases, it becomes possible to eliminate regions that are not scanned due to errors or the like. Moreover, by narrowing the tracking range in the x' direction, the scanning range Scanx in the x' direction can be defined as Scanx≤(L−Δ).

Figure 18A:
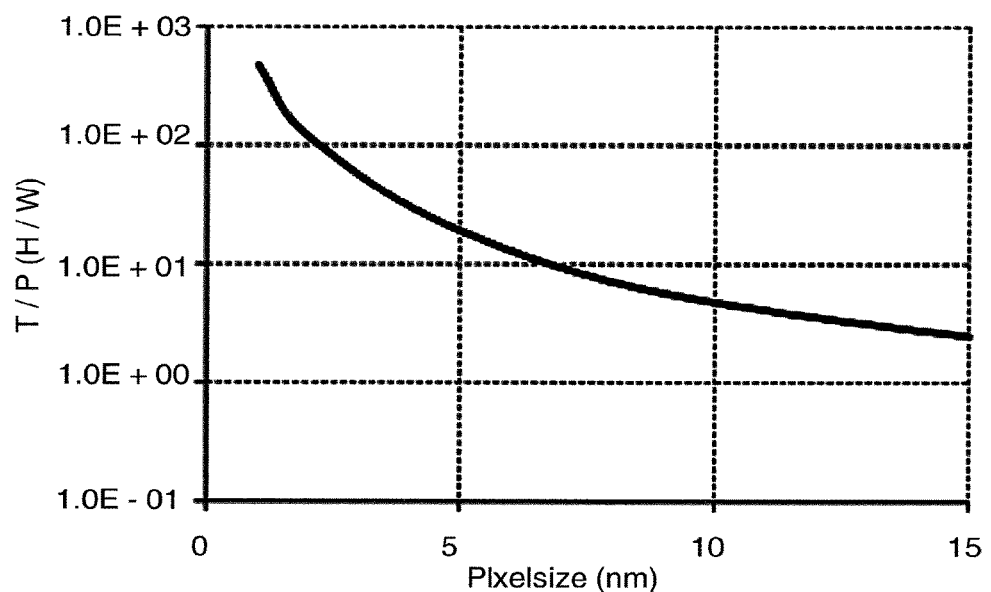
FIGS. 18A and 18B show an example of a relation between a pixel size and a throughput in a comparative example 2 to the first embodiment.
Figure 18B:
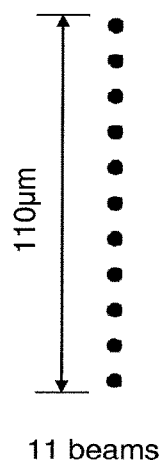

FIGS. 18A and 18B show an example of a relation between a pixel size and a throughput in a comparative example 2 to the first embodiment.

Figure 19A:
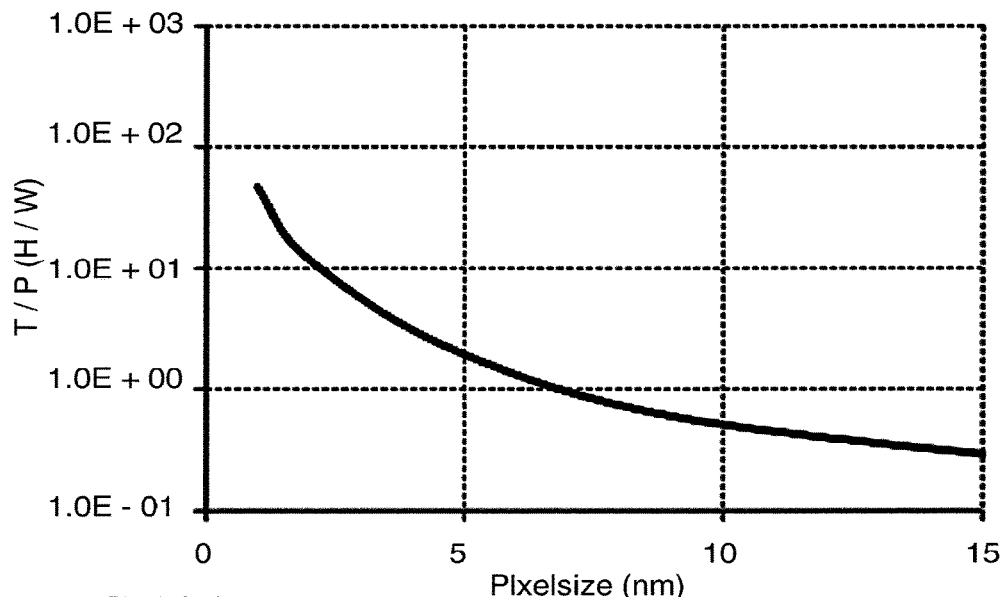
FIGS. 19A and 19B show an example of a relation between a pixel size and a throughput in the first embodiment.
Figure 19B:
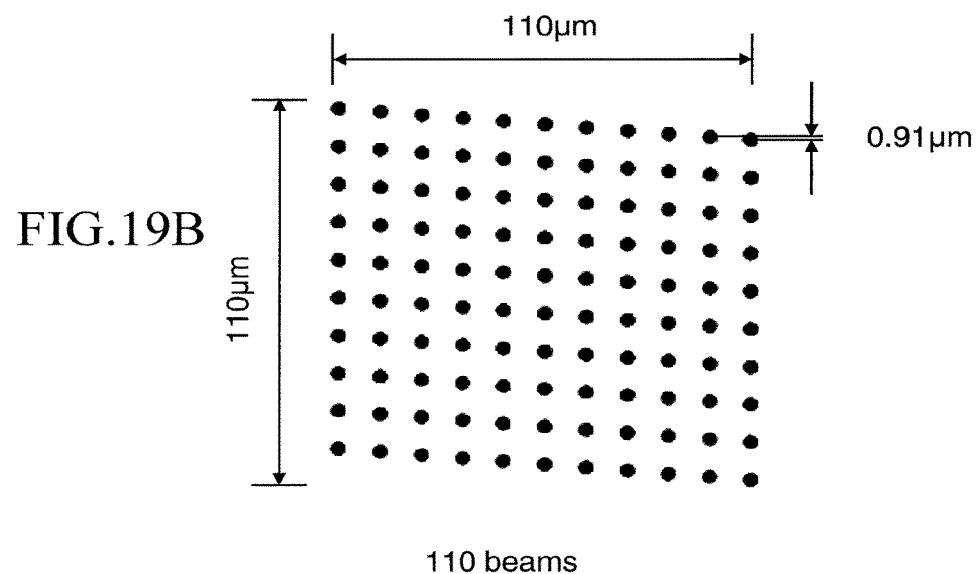

FIGS. 19A and 19B show an example of a relation between a pixel size and a throughput in the first embodiment.

In the comparative example 2, as shown in FIG. 18B, multi-beams composed of 1×11 beams are used where eleven beams are aligned in one column in the y direction. FIG. 18A shows the throughput depending on the pixel size in the case of performing a scanning operation while continuously moving the XY stage 105 in the −x direction using the multi-beams of one column shown in FIG. 18B. The inspection time (H/W) per substrate can be shortened by increasing the pixel size (increasing the beam diameter) irradiated with one beam, thereby improving the throughput (T/P). According to the first embodiment, as shown in FIG. 19B, multi-beams composed of 11×11 beams are used where each beam position in each of the columns, in which eleven beams are aligned in the y direction, is shifted by L/m in the y direction from the beam position of a corresponding one of eleven beams in an adjacent column. FIG. 19A shows the throughput depending on the pixel size in the case of performing a scanning operation while continuously moving the XY stage 105 in the −x direction using the multi-beams composed of 11×11 beams shown in FIG. 19B. The inspection time (H/W) per substrate can be further shortened compared to the comparative example 2 by increasing the pixel size (increasing the beam diameter) irradiated with one beam, thereby further improving the throughput (T/P) compared to the comparative example 2. Such a result can be obtained in the first embodiment because the beams arranged in the x direction do not overlap with each other in the movement direction of the XY stage 105. Similarly, such a result can also be obtained in the second and third embodiments.

In the above description, each " . . . circuit" includes a processing circuitry. As the processing circuitry, for example, an electric circuit, computer, processor, circuit board, quantum circuit, semiconductor device, or the like can be used. Each " . . . circuit" may use a common processing circuitry (same processing circuitry), or different processing circuitries (separate processing circuitries). A program for causing a processor to execute processing may be stored in a recording medium, such as a magnetic disk drive, magnetic tape drive, FD, ROM (Read Only Memory), etc.

Embodiments have been explained referring to specific examples described above. However, the present invention is not limited to these specific examples.

While the apparatus configuration, control method, and the like not directly necessary for explaining the present invention are not described, some or all of them can be selectively used on a case-by-case basis when needed.

In addition, any other electron beam inspection apparatus and electron beam inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electron beam inspection apparatus comprising:
a stage configured to mount a substrate to be inspected thereon and to be continuously movable;
an electron beam column configured, while the stage continuously moves in a predetermined direction, to scan the substrate by irradiating the substrate with multi-beams composed of a plurality of first electron beams in a plurality of beam rows, in each of which corresponding beams of the plurality of first electron beams are arranged at a same pitch in a straight line, such that a center of each of irradiation regions irradiated with the multi-beams does not overlap with other irradiation regions of the irradiation regions in a direction parallel to a movement direction of the stage; and
a detector configured to detect a secondary electron emitted from the substrate due to irradiation of the multi-beams on the substrate, wherein
the electron beam column scans the substrate by deflecting the multi-beams such that a size in the movement direction of the stage, with respect to each of deflection regions for deflecting the multi-beams, differs from a size in a direction orthogonal to the movement direction of the stage.

2. The apparatus according to claim 1, wherein the electron beam column includes
an emission source configured to emit a second electron beam, and
a shaping aperture array substrate, in which a plurality of openings are two-dimensionally formed such that the center of the each of the irradiation regions of the plurality of first electron beams does not overlap with the other irradiation regions of the irradiation regions in the movement direction of the stage moving continuously, and in a manner such that the plurality of openings are arranged at a same pitch in a plurality of straight lines arrayed in parallel to each other at a same interval, configured to form the multi-beams composed of the plurality of first electron beams by irradiating a whole of the plurality of openings with the second electron beam so as to make portions of the second electron beam individually pass through a corresponding one of the plurality of openings.

3. The apparatus according to claim 1, wherein the electron beam column includes an electron optical system configured to rotate an image of the multi-beams so that the center of the each of the irradiation regions of the multi-beams does not overlap with the other irradiation regions of the irradiation regions in the movement direction of the stage moving continuously.

4. The apparatus according to claim 1, wherein the multi-beams are arranged in a matrix, and while a surface of the substrate is scanned, the stage continuously moves in a direction in which the plurality of first electron beams of the multi-beams arranged in the matrix do not overlap with each other.

5. The apparatus according to claim 1, wherein a size obtained by dividing a pitch between beams in the direction orthogonal to the movement direction of the stage by a number of beams aligned in the movement direction of the stage is the size of the deflection region in the direction orthogonal to the movement direction of the stage.

6. The apparatus according to claim 5, wherein a pitch between beams in the movement direction of the stage is the size of the deflection region in the movement direction of the stage.

7. The apparatus according to claim 6, wherein each of the multi-beams is deflected in the movement direction of the stage and the direction orthogonal to the movement direction of the stage, in the deflection region corresponding to the each of the plurality of the multi-beams.

8. The apparatus according to claim 7, wherein a deflection amount of the each of the multi-beams in the movement direction of the stage differs from a deflection amount of the each of the multi-beams in the direction orthogonal to the movement direction of the stage, in the deflection region corresponding to the each of the plurality of the multi-beams.

9. The apparatus according to claim 1, wherein in a case where each of the multi-beams scans the deflection region corresponding to the each of the multi-beams, whose size in the movement direction of the stage differs from size in the direction orthogonal to the movement direction of the stage, the multi-beams are collectively scanned in a same direction.

10. An electron beam inspection method comprising:
scanning, while a stage on which a substrate is placed continuously moves, the substrate with multi-beams composed of a plurality of first electron beams in a plurality of beam rows, in each of which corresponding beams of the plurality of first electron beams are arranged at a same pitch in a straight line, such that a center of each of irradiation regions of the multi-beams does not overlap with other irradiation regions of the irradiation regions in a direction parallel to a movement direction of the stage; and
detecting a secondary electron emitted from the substrate due to irradiation of the multi-beams on the substrate, wherein the scanning the substrate is performed by deflecting the multi-beams such that a size in the movement direction of the stage, with respect to each of deflection regions for deflecting the multi-beams, differs from a size in a direction orthogonal to the movement direction of the stage.

* * * * *